US008729012B2

(12) United States Patent
Lee et al.

(10) Patent No.: US 8,729,012 B2
(45) Date of Patent: May 20, 2014

(54) CONTROLLABLE ASSEMBLY AND DISASSEMBLY OF NANOPARTICLE SYSTEMS VIA PROTEIN AND DNA AGENTS

(75) Inventors: Soo-Kwan Lee, Seoul (KR); Oleg Gang, Setauket, NY (US); Daniel van der Lelie, Shoreham, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 542 days.

(21) Appl. No.: 12/995,919

(22) PCT Filed: Jun. 2, 2009

(86) PCT No.: PCT/US2009/045983
§ 371 (c)(1),
(2), (4) Date: Apr. 25, 2011

(87) PCT Pub. No.: WO2009/149091
PCT Pub. Date: Dec. 10, 2009

(65) Prior Publication Data
US 2011/0196130 A1  Aug. 11, 2011

Related U.S. Application Data

(60) Provisional application No. 61/058,037, filed on Jun. 2, 2008.

(51) Int. Cl.
*C07K 14/00* (2006.01)
(52) U.S. Cl.
USPC ............................ 514/2; 424/491; 977/728
(58) Field of Classification Search
None
See application file for complete search history.

(56) References Cited

U.S. PATENT DOCUMENTS

| 6,361,944 | B1 | 3/2002 | Mirkin et al. |
| 6,767,702 | B2 | 7/2004 | Mirkin et al. |
| 6,878,523 | B2 | 4/2005 | Nelson et al. |
| 6,974,669 | B2 | 12/2005 | Mirkin et al. |
| 7,045,285 | B1 | 5/2006 | Kayyem et al. |
| 2002/0172953 | A1 | 11/2002 | Mirkin et al. |
| 2003/0198956 | A1 | 10/2003 | Makowski et al. |
| 2003/0215903 | A1 | 11/2003 | Hyman et al. |
| 2005/0130174 | A1 | 6/2005 | Bao et al. |
| 2007/0054337 | A1 | 3/2007 | Ferning et al. |
| 2007/0134420 | A1 | 6/2007 | Koberstein et al. |

FOREIGN PATENT DOCUMENTS

| WO | W02004042084 | 5/2004 |
| WO | W02004046687 | 6/2004 |
| WO | W02008127281 | 10/2008 |

OTHER PUBLICATIONS

Hazarika et al., "Reversible switching of DNA-gold nanoparticle aggregation", Agnew. Chem. Int. Ed. 43: 6469-6471 (2004).*
Niemeyer, "Nanoparticles, Proteins, and Nucleic Acids: Biotechnology meets Material Science", Angew. Chem. Int. Ed. 40: 4128-4158 (2001).*
International Search Report of International Application PCT/US2009/045983—Date of Completion of Search: Oct. 22, 2009, 8 pages.
International Preliminary Report on Patentability of the International Searching Authority of International Application No. PCT/US2009/045983—Date mailed: Oct. 26, 2009, 10 pages.
Written Opinion of the International Searching Authority of International Application No. PCT/US2009/045983—Date mailed: Oct. 26, 2009, 9 pages.
Alivisatos, A., et al., "Organization of 'Nanocrystal Molecules' Using DNA," *Nature*, vol. 382 pp. 609-611, 1996.
Bath, J., et al., "DNA Nanomachines," *Nature Nanotechnology*, vol. 2, pp. 275-284, 2007.
Bélanger, P., et al., "Facile Preparations of 4-Fluororesorcinol," *Canadian Journal of Chemistry*, vol. 66, pp. 1479-1482, 1988, [online] [Retrieved Jan. 6, 2012] from the Internet <URL://www.nrcresearchpress.com>.
Bulsink, H., et al., "DNA-Binding Properties of Gene-5 Protein Encoded by Bacteriophage M13, 2. Further Characterization of the Different Binding Modes for Poly- and Oligodeoxynucleic Acids," *European Journal of Biochemistry*, vol. 176, pp. 597-608, 1988.
Cao, G., "*Nanostructures & Nanomaterials: Synthesis, Properties and Applications*," (London, Imperial College Press, 2004) pp. 263-265 with title page and bibliographic page.
Cao, G., "*Nanostructures & Nanomaterials: Synthesis, Properties and Applications*," (London, Imperial College Press, 2004) pp. 396-397 with title page and bibliographic page.
Chorny, M., et al., "Magnetically Driven Plasmid DNA Delivery With Biodegradeable Polymeric Nanoparticles," *The FASEB Journal*, vol. 21, pp. 2510-2519, 2007 and supplementary material, 2 pages [online] [retrieved Apr. 16, 2012] from the Internet <URL://www.fasebj.org/content/21/10/2510/suppl/DC1>.
Dubertret, B., et al., "Single-Mismatch Detection Using Gold-Quenched Fluorescent Oligonucleotides," *Nature Biotechnology*, vol. 19, pp. 365-370, 2001.
Elghanian, R., et al., "Selective Colorimetric Detection of Polynucleotides Based on the Distance-Dependent Optical Properties of Gold Nanoparticles," *Science*, vol. 277, pp. 1078-1081, 1997.
Elimelech, M., et al., "*Particle Deposition & Aggregation: Measurement, Modelling and Simulation*," (Oxford, Butterworth-Heinemann Ltd, 1995) pp. 9-32, with cover page, title page and bibliographic page.
Elimelech, M., et al., "*Particle Deposition & Aggregation: Measurement, Modelling and Simulation*," (Oxford, Butterworth-Heinemann Ltd, 1995) pp. 33- 67, with cover page, title page and bibliographic page.

(Continued)

*Primary Examiner* — Anand Desai
(74) *Attorney, Agent, or Firm* — Dorene M. Price; Lars O. Husebo

(57) ABSTRACT

The invention relates to the use of peptides, proteins, and other oligomers to provide a means by which normally quenched nanoparticle fluorescence may be recovered upon detection of a target molecule. Further, the inventive technology provides a structure and method to carry out detection of target molecules without the need to label the target molecules before detection. In another aspect, a method for forming arbitrarily shaped two- and three-dimensional protein-mediated nanoparticle structures and the resulting structures are described. Proteins mediating structure formation may themselves be functionalized with a variety of useful moieties, including catalytic functional groups.

13 Claims, 16 Drawing Sheets

(56) References Cited

OTHER PUBLICATIONS

Folmer, R., et al., "A Model of the Complex Between Single-Stranded DNA and the Single-Stranded DNA Binding Protein Encoded by Gene V of Filamentous Bacteriophage M13," *Journal of Molecular Biology*, vol. 240, pp. 341-357, 1994.

Gao, X., et al., "Peptide-Based Nanotubes and Their Applications in Biotechnology," *Advanced Materials*, vol. 17, pp. 2037-2050, 2005.

He, L., et al., "Colloidal Au-Enhanced Surface Plasmon Resonance for Ultrasensitive Detection of DNA Hybridization," *Journal of the American Chemical Society*, vol. 122, pp. 9071-9077, 2000, and supplementary information pp. S2-S6, [online] [retrieved Apr. 18, 2012] from the Internet <URL: //pubs.acs.org/doi/suppl/10.1021/ja001215b/suppl_file/ja001215b_s.pdf>.

Hu, M., et al., "Assembly of Nanoparticle-Protein Binding Complexes: From Monomers to Ordered Arrays," *Angewandte Chemie*, vol. 119, pp. 5203-5206, 2007.

Kerman, K., et al., "Modification of *Escherichia coli* Single-Stranded DNA Binding Protein With Gold Nanoparticles for Electrochemical Detection of DNA Hybridization," *Analytica Chimica Acta*, vol. 510, pp. 169-174, 2004.

Lee, S., et al., "Ordering of Quantum Dots Using Geneticaly Engineered Viruses," *Science*, vol. 296, pp. 892-895, 2002, and supplementary information (3 pages) [online] [retrieved Apr. 16, 2012] from the Internet <URL://www.sciencemag.org/content/suppl/2002/05/01/296.5569.892.DC1/Lee.pdf>.

Lee, S., et al., "Controllable g5p-Protein-Directed Aggregation of ssDNA-Gold Nanoparticles," *Langmuir*, vol. 25, pp. 657-660, 2009, and supplementary information pp. 1-5 [online] [retrieved Apr. 16, 2012] from the Internet <URL://pubs.acs.org/doi/suppl/10.1021/la803596q/suppl_file/la803596q_si_001.pdf>.

Lim, I., et al., "Assembly/Disassembly of DNA-Au Nanoparticles: A Strategy of Intervention," *Research Letters in Nanotechnology*, vol. 2008, 4 pages, 2008.

Mao, C., et al., "A Nanomechanical Device Based on the B-Z Transition of DNA," *Nature*, vol. 397, pp. 144-146, 1999.

Mao, C., et al., "Virus-Based Toolkit for the Directed Synthesis of Magnetic and Semiconducting Nanowires," *Science*, vol. 303, pp. 213-217, 2004.

Mattoussi, H., et al., "Self-Assembly of CdSe—ZnS Quantum Dot Bioconjugates Using an Engineered Recombinant Protein," *Journal of the American Chemical Society*, vol. 122, pp. 12142-12150, 2000.

Maye, M., et al., "A Simple Method for Kinetic Control of DNA-Induced Nanoparticle Assembly," *Journal of the American Chemical Society*, vol. 128, pp. 14020-14021, 2006, and supplementary information pp. S1-S10 [online] [retrieved Apr. 17, 2012] from the Internet <URL://pubs.acs.org/doi/suppl/10.1021/ja0654229/suppl_file/ja0654229si20060921_055711.pdf>.

Maye, M., et al., "DNA-regulated Micro- and Nanoparticle Assembly," *Small*, vol. 3, pp. 1678-1682, 2007.

Mirkin, C., et al., "A DNA-Based Method for Rationally Assembling Nanoparticles Into Macroscopic Materials," *Nature*, vol. 382, pp. 607-609, 1996.

Mou, T., et al., "The Binding Affinity of Ff Gene 5 Protein Depends on the Nearest-Neighbor Composition of the ssDNA Substrate," *Biophysical Journal*, vol. 76, pp. 1537-1551, 1999.

Mou, T., et al., "Binding and Reversible Denaturation of Double-Stranded DNA by Ff Gene 5 Protein," *Biopolymers*, vol. 70, pp. 637-648, 2003.

Nam, J., et al., "Bio-Barcodes Based on Oligonucleotide-Modified Nanoparticles," *Journal of the American Chemical Society*, vol. 124, pp. 3820-3821, 2002.

Niemeyer, C., et al., "Self-Assembly of DNA-Streptavidin Nanostructures and Their Use as Reagents in Immuno-PCR," *Nucleic Acids Research*, vol. 27, pp. 4553-4561, 1999, and supplementary information pp. 1-8 [online] [retrieved Apr. 24, 2012] from the Internet <URL.//nar.oxfordjournals.org/content/suppl/2000/04/08/27.23.4553.DC1/gkc664_sup.pdf>.

Niemeyer, C., "DNA-Protein Nanostructures," in *Nanobiotechnology: Concepts, Applications and Perspectives*, Niemeyer, C. and Mirkin, C.A. Eds., (Weinheim, Wiley-VCH Verlag GmbH & Co., KGaA) pp. 227-243, with title page and bibliographic page.

Nykypanchuk, D., et al., "DNA-Guided Crystalization of Colloidal Nanoparticles," *Nature*, vol. 451, pp. 549-552, 2008.

Olah, G., et al., "Structures of fd Gene 5 Protein-Nucleic Acid Complexes: A Combined Solution Scattering and Electron Microscopy Study," *Journal of Molecular Biology*, vol. 249, pp. 576-594, 1995.

Park, S., et al., "Array-Based Electrical Detection of DNA With Nanoparticle Probes," *Science*, vol. 295, pp. 1503-1506, 2002 and supplementary information pp. 1-2 [online] [retrieved Jan. 9, 2012] from the Internet <URL://www.sciencemag.org/content/295/5559/1503/suppl/DC1>.

Sarikaya, M., et al., "Molecular Biomimetics: Nanotechnology Through Biology," *Nature Materials*, vol. 2, pp. 577-585, 2003.

Schulze, A., et al., "Navigating Gene Expression Using Microarrays—A Technology Review," *Nature Cell Biology*, vol. 3, pp. E190-E195, 2001.

Shengqi, W., et al., "A New Fluorescent Quantitative Polymerase Chain Reaction Technique," *Analytical Biochemistry*, vol. 309 pp. 206-211, 2002.

Stoermer, R., et al., "Coupling Molecular Beacons to Barcoded Metal Nanowires for Multiplexed, Sealed Chamber DNA Bioassays," *Journal of the American Chemical Society*, vol. 128, pp. 16892-16903, 2006, and supplementary information pp. S1-S3 [online] [retrieved Apr. 16, 2012] from the Internet <URL://pubs.acs.org/doi/suppl1/10.1021/ja0658261/suppl_file/ja0658261si20061018_094845.pdf>.

Storhoff, J., et al., "What Controls the Optical Properties of DNA-Linked Gold Nanoparticle Assemblies?" *Journal of the American Chemical Society*, vol. 122, pp. 4640-4650, 2000.

Taton, T., et al., "Scanometric DNA Array Detection with Nanoparticle Probes," *Science*, vol. 289, pp. 1757-1760, 2000, [online] [retrieved Jan. 9, 2012] from the Internet <URL://www.sciencemag.org/content/289/5485/1757.full.pdf>.

Taton, T., et al., "Two-Color Labeling of Oligonucleotide Arrays Via Size-Selective Scattering of Nanoparticle Probes," *Journal of the American Chemical Society*, vol. 123, pp. 5164-5165, 2001 and supplementary information pp. S1-S11 [online] [retrieved Apr. 17, 2012] from the Internet <URL: //pubs.acs.org/doi/suppl/10.1021/ja0102639/suppl_file/ja0102639_s.pdf>.

Terwilliger, T., "Gene V Protein Dimerization and Cooperativity of Binding to Poly(dA)," *Biochemistry*, vol. 35, pp. 16652-16664, 1996.

Thaxton, C.S. et al, "DNA-Gold Nanoparticle Conjugates," in *Nanobiotechnology: Concepts, Applications and Perspectives*, Niemeyer, C. and Mirkin, C.A. Eds., (Weinheim, Wiley-VCH Verlag GmbH & Co., KGaA) pp. 288-307, with title page and bibliographic page.

Thompson, T., et al., "Circular Dichroism and Electron Microscopy of a Core Y61F Mutant of the F1 Gene 5 Single-Stranded DNA-Binding Protein and Theoretical Analysis of CD Spectra of Four Tyr → Phe Substitutions," *Biochemistry*, vol. 37, pp. 7463-7477, 1998, and supplementary information pp. 1-7 [online] [retrieved Apr. 17, 2012] from the Internet <URL://pubs.acs.org/doi/suppl/10.1021/bi972545k/suppl_file/bi7463.pdf>.

Tugwood, J., et al., "The Mouse Peroxisome Proliferator Activated Receptor Recognizes a Response Element in the 5' Flanking Sequence of the Rat Acyl CoA Oxidase Gene," *The European Molecular Biology Journal*, vol. 11, pp. 433-439, 1992.

Wen, J., et al., "The Ff Gene Single-Stranded DNA-Binding Protein Binds to the Transiently Folded Form of an Intramolecular G-Quadruplex," *Biochemistry*, vol. 41, pp. 11438-11448, 2002.

(56) References Cited

OTHER PUBLICATIONS

Wen, J., et al., "Ff Gene 5 Single-Stranded DNA-Binding Protein Assembles on Nucleotides Constrained by a DNA Hairpin," *Biochemistry*, vol. 43, pp. 2622-2634, 2004.

Whaley, S., et al., "Selection of Peptides With Semiconductor Binding Specificity for Directed Nanocrystal Assembly," *Nature*, vol. 405, pp. 665-668, 2000.

Yan, H., et al., "A Robust DNA Mechanical Device Controlled by Hybridization Topology," *Nature*, vol. 415, pp. 62-65, 2002, and supplementary information pp. 1-10, [online] [retrieved Apr. 16, 2012] from the Internet <URL://www.nature.com/nature/journal/v415/n6867/full/415062a.html>.

Zhang, Y., et al., "Functionalized Carbon Nanotubes for Detecting Viral Proteins," *Nano Letters*, vol. 7, pp. 3086-3091, 2007, and supplementary information pp. 1-15, [online] [retrieved Apr. 16, 2012] from the Internet <URL://pubs.acs.org/doi/suppl/10.1021/nl071572l/suppl_file/nl071572lsi20070826_014724.pdf>.

Zhong, P., et al., "Synthesis of Mercaptoethylamine-Coated CdSe/CdS Nanocrystals and Their Use for DNA Probe," *Analytical Sciences*, vol. 23, pp. 1085-1089, 2007.

\* cited by examiner

SEQUENCE LISTING

```
<160> NUMBER OF SEQ ID NOS: 9

<210> SEQ ID NO 1
<211> LENGTH: 30
<212> TYPE: DNA
<213> ORGANISM: Artificial Sequence
<220> FEATURE:
<223> OTHER INFORMATION: Artificial ss-DNA Sequence
<220> FEATURE:
<221> NAME/KEY: misc_feature
<222> LOCATION: (1)..(1)
<223> OTHER INFORMATION: 5'-HS-C3H6-
```

<400> SEQUENCE: 1
tttttttttt tttttttaacc taaccttcat                              30

<210> SEQ ID NO 2
<211> LENGTH: 15
<212> TYPE: DNA
<213> ORGANISM: Artificial Sequence
<220> FEATURE:
<223> OTHER INFORMATION: complementary single-stranded DNA

<400> SEQUENCE: 2
atgaaggtta ggtta                                               15

<210> SEQ ID NO 3
<211> LENGTH: 18
<212> TYPE: DNA
<213> ORGANISM: Artificial Sequence
<220> FEATURE:
<223> OTHER INFORMATION: non-complementary single-stranded DNA

<400> SEQUENCE: 3
aatattgata aggatagc                                            18

<210> SEQ ID NO 4
<211> LENGTH: 30
<212> TYPE: DNA
<213> ORGANISM: Artificial Sequence
<220> FEATURE:
<223> OTHER INFORMATION: complementary single-stranded DNA
<220> FEATURE:
<221> NAME/KEY: misc_feature
<222> LOCATION: (1)..(1)
<223> OTHER INFORMATION: 5'-HS-C3H6

<400> SEQUENCE: 4
tttttttttt tttttatgaa ggttaggtta                               30

<210> SEQ ID NO 5
<211> LENGTH: 33
<212> TYPE: DNA
<213> ORGANISM: Artificial Sequence
<220> FEATURE:
<223> OTHER INFORMATION: bacteriophage M13 g5p gene primer

<400> SEQUENCE: 5
taattccata tgattaaagt tgaaattaaa cca                           33

<210> SEQ ID NO 6
<211> LENGTH: 35
<212> TYPE: DNA
<213> ORGANISM: Artificial Sequence
<220> FEATURE:
<223> OTHER INFORMATION: bacteriophage M13 g5p gene primer

<400> SEQUENCE: 6
tagcttgctc ttccgcactt agccggaacg aggcg                         35

<210> SEQ ID NO 7
<211> LENGTH: 66
<212> TYPE: DNA
<213> ORGANISM: Artificial Sequence
<220> FEATURE:
<223> OTHER INFORMATION: single-stranded DNA

<400> SEQUENCE: 7
gaccacatac cgcaccatct tttttttttt tttttttttt tttttttttt tctgctacga    60

-continued

```
gacttc                                                              66

<210> SEQ ID NO 8
<211> LENGTH: 51
<212> TYPE: DNA
<213> ORGANISM: Artificial Sequence
<220> FEATURE:
<223> OTHER INFORMATION: single-stranded DNA

<400> SEQUENCE: 8
tttttttttt tttttttttt tttttttttt ttgatggtgc ggtatgtggt c            51

<210> SEQ ID NO 9
<211> LENGTH: 15
<212> TYPE: DNA
<213> ORGANISM: Artificial Sequence
<220> FEATURE:
<223> OTHER INFORMATION: complementary single-stranded DNA

<400> SEQUENCE: 9
gaagtctcgt agcag                                                    15
```

CONTROLLABLE ASSEMBLY AND DISASSEMBLY OF NANOPARTICLE SYSTEMS VIA PROTEIN AND DNA AGENTS

This application is a national phase entry under 35 U.S.C. 371 of International Application Number PCT/US2009/045983, filed on Jun. 2, 2009, entitled "CONTROLLABLE ASSEMBLY AND DISASSEMBLY OF NANOPARTICLE SYSTEMS VIA PROTEIN AND DNA AGENTS", which claims priority to U.S. Provisional Patent Application Number 61/058,037, filed on Jun. 2, 2008, all of which are hereby incorporated by reference.

This invention was made with Government support under contract number DE-AC02-98CH10886, awarded by the U.S. Department of Energy. The Government has certain rights in the invention.

BACKGROUND OF THE INVENTION

The invention relates to the use of peptides, proteins, and other oligomers to provide a means by which normally quenched nanoparticle fluorescence may be recovered upon detection of a target molecule. Further, the invention provides a structure and method to carry out detection of target molecules without the need to label the target molecules before detection.

Nanotechnology research and its findings have been studied in many different research areas and are being applied for the development of scientific and industrial technologies, such as nano electronics, sensors, and catalysts. Frontier energy, medical, and security-related nanotechnology will depend on the integration and optimization of nanoparticle-based technologies and biological sciences to design hybrid materials for increasingly cleaner and more efficient energy conversion and storage, as well as biological sensors having increased sensitivity. Such integration requires not only the precise control of nanoparticle size, shape, composition, and surface properties, but also the ability to self-assemble and dissociate nanoparticles with controlled kinetics and final assembly morphology under conditions tolerated by biological systems.

Currently, the self-assembly of nanoparticles with metallic (Au, Ag, Pt), semiconductive (CdSe, CdS, ZnS, GaAs), and magnetic ($Fe_2O_3$) properties using biological building blocks is achieved by two main approaches: (i) DNA-based systems and (ii) protein- (peptide-) based systems. The remarkable specificity and programmable interactions of DNA allows self-assembly of DNA-conjugated nanoparticles and construction of complex architectures. Their complexity and functionality may be extended via the incorporation of proteins that function as biological sensors or as organizers of complex scaffolds. The DNA-based self-assembly systems have shown great potential as biological sensors. Specific binding of peptides to inorganic surfaces has been demonstrated, and these peptides can be selected by using phage display system. Also, the peptides have been successfully used for the construction of nanostructures and self-assembly of inorganic nanoparticles. Due to the functional variety of proteins, the combination of DNA- and protein-based systems is receiving considerable attention to design functional hybrid nanomaterials.

The self-assembly of nanoparticles and programmed complex architectures using DNA have been demonstrated. DNA-induced self-assembly of nanoparticles was first introduced in 1996 by pioneering papers of Mirkin and co-workers, "A DNA-based method for rationally assembling nanoparticles into macroscopic materials," Nature, 382(6592): p. 607-609, 1996, and Alivisatos and co-workers, "Organization of 'nanocrystal molecules' using DNA," Nature, 382(6592): p. 609-611, 1996, both of which articles are hereby incorporated by reference in their entirety. The ability of specific hybridization of DNA was utilized for self-assembly of nanoparticles on which single stranded DNA (ssDNA) is chemically immobilized. Aggregation was obtained by adding a single stranded linker DNA whose ends were complementary to the ssDNAs conjugated to the particles. The aggregation of ssDNA conjugated nanoparticles is accompanied by changes of physical and optical properties, and was applied to detect DNA. Addition of a DNA fragment complementary to the linker results in dissociation of the aggregates. Alternatively, the system can be designed such that the DNA fragments to be detected function as the linker. The melting properties of DNA, which depend on sequence and length, make it possible to reverse the self-assembly of the aggregates by increasing temperatures (FIG. 1). The sequence-dependent melting properties allow detection of single point mutation using ssDNA-conjugated nanoparticles.

Gold-nanoparticle quenched fluorescent oligonucleotides, that are designed for complementary binding at their 3' and 5' ends to form a hairpin structure, have been used as molecular beacons for detecting target DNA that hybridizes to the hairpin structure, resulting in emission of the quenched fluorescence.

Microarray technology is used on a routine basis for high through-put quantification of large numbers of different DNA or RNA fragments. The array-based systems require labeling of target DNA, or RNA, via synthesis of C-DNA. ssDNA-conjugated nanoparticles have been used as candidates to probe their target molecules.

In addition, the specific interaction of DNA has been used to create DNA building blocks, and assembly of the building blocks to construct sophisticated geometries and morphologies.

SUMMARY

While the above mentioned systems require hybridization of complementary DNA strands as a prerequisite for correct assembly, and disassembly is obtained by melting of the DNA at elevated temperatures, the processes will often result in the irreversible inactivation of functional moieties, such as proteins. The inventive method allows for controllable assembly of non-complementary single stranded DNA-(ssDNA-) conjugated nanoparticles, using the gene 5 protein (g5p) as a molecular "glue" binding to two anti-parallel ssDNA strands. Control of assembly kinetics of particle aggregates can be obtained via sequence-specific hybridization with complementary ssDNA (C-ssDNA), while the size of aggregates is controlled by adjustment of the g5p concentration. The controllable disassembly of the g5p-ssDNA complex may be triggered by hybridization with C-ssDNA, which allows regulation of assembly kinetics and effective decom-position of particle aggregates at room or physiological temperatures. In addition, the g5p protein allows for the construction of functional, recombinant derivatives that contain poly-histidine or other affinity tags that allow these proteins to specifically bind to surfaces of nanoparticles. This allows control of both assembly and disassembly of nanoparticles without thermal treatment, and easy incorporation of proteins into DNA-based nanostructures, conferring the potential to design complex nanomaterials.

The invention relates to the use of peptides, proteins, and other oligomers to provide a means by which normally quenched nanoparticle fluorescence may be recovered upon detection of a target molecule. Further, the inventive technology provides a structure and method to carry out detection of target molecules without the need to label the target molecules before detection. In another aspect, a method for forming arbitrarily shaped two- and three-dimensional protein-mediated nanoparticle structures and the resulting structures are described. Proteins mediating structure formation may themselves be functionalized with a variety of useful moieties.

In some embodiments of the invention, a controllable and reversible assembly of nanoparticles using the g5p protein or similar DNA binding proteins is provided. In some variants, the nanoparticles are encapsulated in DNA and/or RNA and the nanoparticles are assembled with a nucleotide binding protein. In other variants, the nanoparticles are encapsulated with a nucleotide binding protein, and the nanoparticles are assembled with DNA and/or RNA. Some embodiments provide a multi-dimensional structure comprising branches of single stranded DNA and/or RNA, nucleotide binding protein, and nanoparticles. Some embodiments of the invention also provide a method or process for preparing a controllable and reversible assembly of nanoparticles using a nucleotide binding protein.

Other embodiments of the invention provide a nucleic acid binding protein-mediated DNA assemblage that comprises non-complementary DNA or RNA strands bound to a nucleotide binding protein.

Still other embodiments of the invention provide a molecular switch which comprises a fluorescent quenched "off" position and a fluorescent emission "on" position, comprising ssDNA bound to fluorescein and a second ssDNA bound to DABCYL. The switch can be turned "on" by hybridizing a complementary ssDNA or ssRNA to either the fluorescein-ssDNA strand or the ssDNA-DABCYL strand.

DETAILED DESCRIPTION

Figure 1:
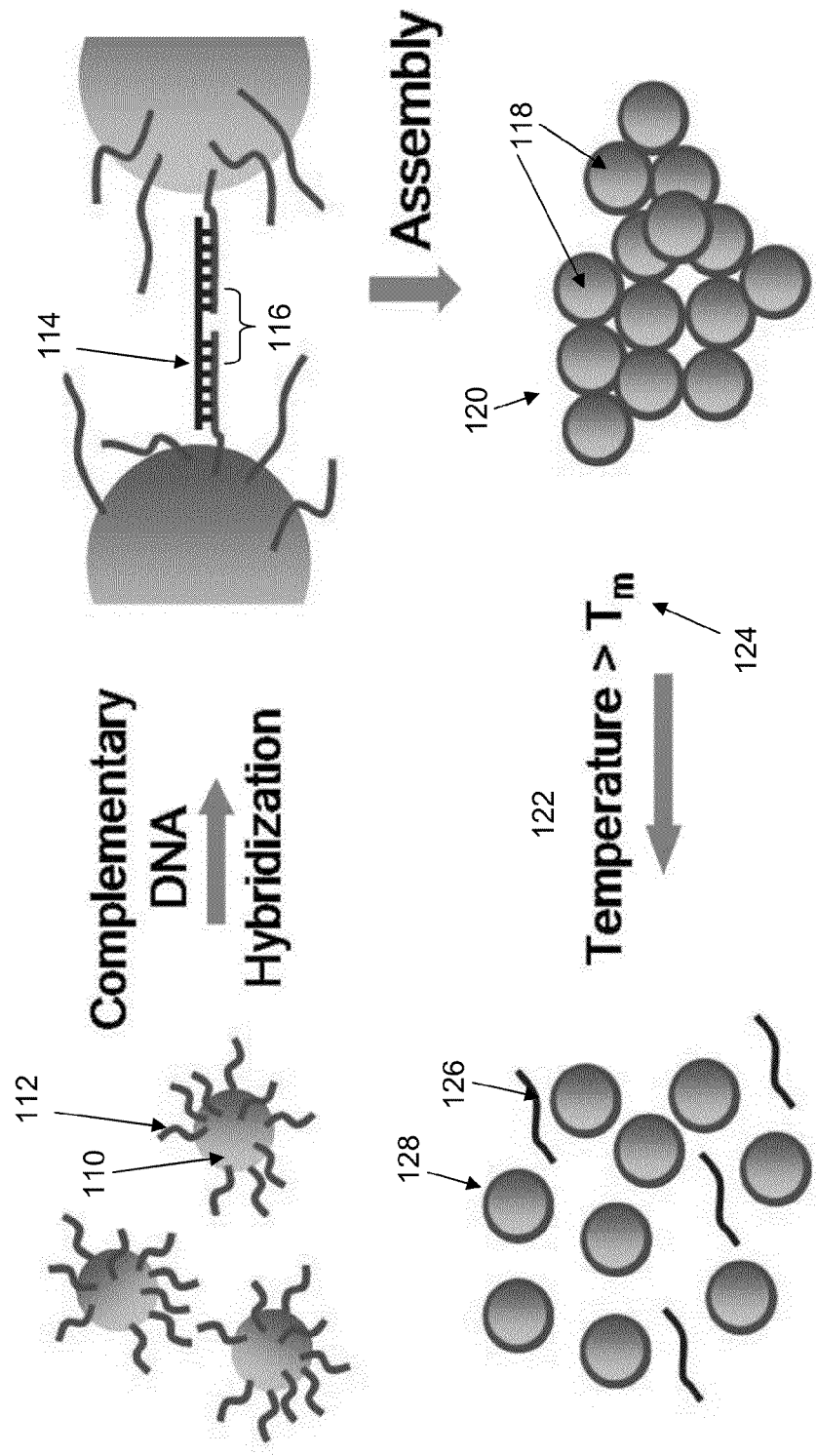
FIG. 1 shows a prior art method for self-assembly and disassembly of ssDNA-conjugated nanoparticles.

In contrast to DNA, proteins have not only specific binding properties, but also abundant catalytic functional properties. The interactions of protein and peptide have been utilized for self-assembly and ordering of nanoparticles. Peptides that have specificity for inorganic compounds (metallic, semiconductive, and magnetic compounds) have been selected using peptide libraries, and have been used successfully for self-assembly of inorganic nanoparticles and biomineralization. Noting the specific interactions between peptides and inorganic surfaces, the inventors suggest that the inorganic nanoparticles may be linked with proteins by genetic engineering of proteins to display peptides.

The combination of the DNA- and protein-based systems is attractive for extension of their applicability as biosensors or organizers of complex scaffolds. Biotin-conjugated DNA has been utilized as a building block for assembly by binding to streptavidin that can cross-link the biotin-conjugated DNA. Antibodies have been used for protein-assisted self-assembly of DNA-conjugated nanoparticles that contain the antibodies' target molecules.

Despite these advances in using both DNA and proteins for the construction of nano-scale materials, there are still many limitations and technical hurdles. DNA requires the proper conditions for the desired hybridization. There are inherent limitations of DNA hybridization such as G-C content, salt concentration, and temperature. The distribution of proteins in the composed structure allows for identical functionality throughout the entire structure with control of kinetics and size of assemblies only when homogenous. During self-assembly of ssDNA-conjugated nanoparticles induced by DNA-hybridization, it is difficult to introduce proteins without chemical modification of the oligonucleotides, e.g. biotinylation, to allow for binding of the protein. The increased temperature can induce irreversible inactivation of biological molecules, especially proteins. Disassembly of the aggregates formed by DNA hybridization requires increases of temperature above the melting temperature, often around 55° C. or above, which can cause limitations of the system to be used in biological environments. To detect target molecules (DNA, RNA) using array-based systems, labeling is a critical, costly, and time-consuming step. Labeling of target molecules requires additional time for sample preparation, limiting quick detection or diagnosis of biological molecules.

Using the gene 5 protein (g5p) as a molecular "glue" binding two anti-parallel non-complementary singled stranded DNA (ssDNA) overcomes many of the limitations for fabricating nanoscale materials by combination of DNA and proteins mentioned above. Additional hybridization with complementary ssDNA (C-ssDNA), which triggers the g5p-ssDNA complex to dissociate, may also be used.

An aspect of the invention provides for controllable and reversible assembly of nanoparticles and methods for preparing the same.

In some embodiments of the invention, the nanoparticle is metallic. In preferred embodiments, the metal is gold, silver, or platinum. In more preferred embodiments, the nanoparticle is gold. In other embodiments, the nanoparticle is a semiconductor. In some variants, the semiconductor is cadmium selenide, cadmium sulfide, zinc sulfide, or gallium arsenide. In other embodiments, the nanoparticle is magnetic. In some variants, the magnetic nanoparticle comprises iron oxide.

In some embodiments of the nanoparticle assembly, the DNA and/or RNA are single stranded or double stranded. In preferred embodiments, the DNA is single stranded.

In some embodiments the nucleotide binding protein is any protein that can bind to DNA or RNA. In preferred embodiments, the nucleotide binding protein is gene 5 protein (g5p).

In some embodiments, a controllable and reversible assembly of nanoparticles using the g5p protein or similar DNA binding proteins is provided.

In some embodiments, the controllable and reversible nanoparticle assembly comprises nanoparticles encapsulated with non-complementary DNA and/or RNA. In preferred embodiments, nanoparticles encapsulated with non-complementary DNA and/or RNA are bound together by a nucleotide binding protein to form a nanoparticle assembly. In this manner, a controllable and reversible nanoparticle assembly is formed.

In further embodiments of the controllable and reversible nanoparticle assembly, the nanoparticle assembly is disassembled by further combining the nanoparticle assembly with DNA and/or RNA complementary to the non-complementary DNA and/or RNA. In this manner, a controllable and reversible nanoparticle disassembly is achieved.

The inventive method provides for controllable assembly of non-complementary ssDNA-conjugated nanoparticles using the g5p protein or similar DNA binding proteins. Hybridization with low concentrations of C-ssDNA during the assembly phase may be used to regulate assembly kinetics. In addition, C-ssDNA has been used to achieve effective decomposition of particle aggregates at room temperature (FIG. 2) or physiological temperatures. This approach makes it possible to control both assembly and disassembly of nanoparticles without thermal treatment, and to easily incorporate g5p-based hybrid proteins, e.g., containing affinity tags or additional catalytic domains, into DNA-based nanostructures, conferring the potential to design complex nanomaterials.

In some embodiments of the method, a controllable nanoparticle assembly and disassembly process is prepared by encapsulating nanoparticles with DNA and/or RNA; combining the encapsulated nanoparticles with a nucleotide binding protein; and binding the DNA and/or RNA to the nucleotide binding protein. In this manner, a controllable nanoparticle assembly process is prepared.

In some variants of the method, the assembly of nanoparticles is disassembled by further combining the nanoparticle assembly with nucleotides complementary to the non-complementary DNA and/or RNA. In this manner, a controllable nanoparticle disassembly process is achieved.

In some embodiments of the method, a nanoparticle assembly is prepared by functionalizing a plurality of nanoparticles with non-complementary ssDNA; exposing the functionalized nanoparticles to gene 5 protein; and linking at least two strands of the ssDNA with the g5p.

Figure 3:
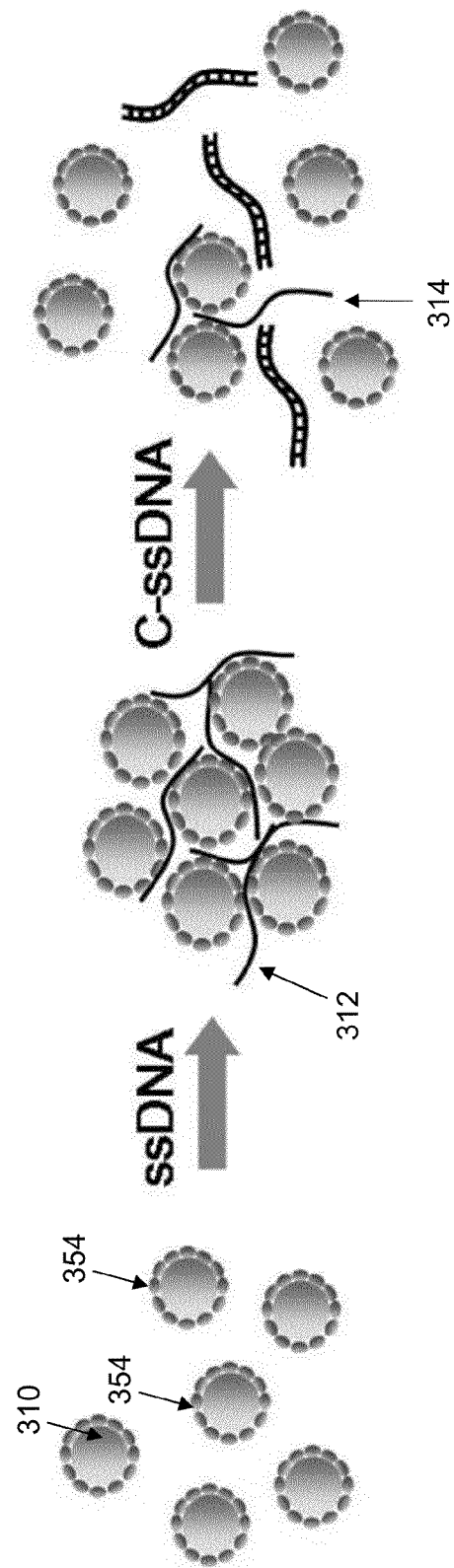
FIG. 3 shows a sketch of ssDNA-mediated assembly and disassembly of g5p-conjugated nanoparticles.

To achieve further sensitive assembly and disassembly of nanoparticles in response to target DNAs, the invention contemplates the use of g5p-conjugated nanoparticles that can be bridged by non-complementary ssDNA and dissociated by sensing its complementary ssDNA (FIG. 3). Poly-histidine tagged g5p will be immobilized on Ni-NTA-conjugated gold nanoparticles to achieve oriented g5p in which the DNA binding sites are active by facing the outer direction of the nanoparticles. Length and shape of DNA may affect the size or morphology of the aggregates. This DNA-mediated control of g5p-conjugated nanoparticles may lead to the design of a smart materials sensor for DNA at biological conditions.

In some embodiments, an assembly of nanoparticles is prepared by functionalizing a plurality of nanoparticles with a nucleotide binding protein; incubating the functionalized nanoparticles with non-complementary DNA and/or RNA; and linking at least two strands of the DNA and/or RNA with the nucleotide binding protein. In this manner, an assembly of nanoparticles is prepared.

Figure 5:
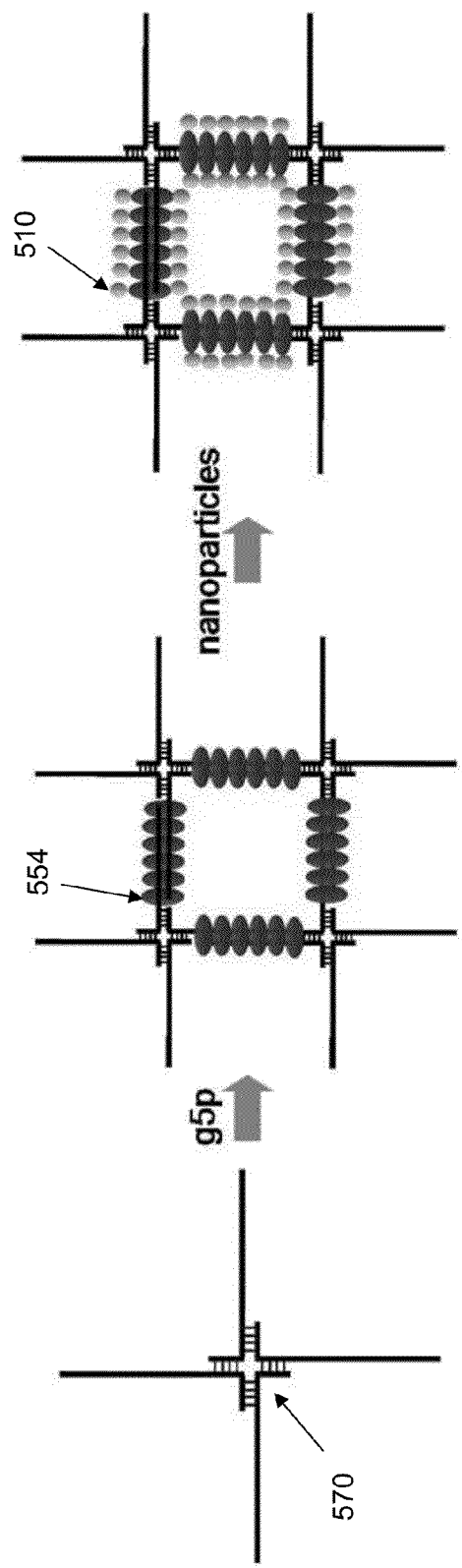
FIG. 5 shows self-assembly of nanoparticles at ordered peptide-conjugated g5p and DNA.

To achieve precise self-assembly of nanoparticles in multiple dimensions, the complex of structured DNA and peptide-tagged g5p is proposed, in which the peptide can specifically bind to nanoparticles. The organization of g5p by binding to a ssDNA region may result in the formation of a DNA scaffold from simple building blocks, while the affinity tag can be used for further ordering of nanoparticles on the DNA scaffold (FIG. 5). This method may make possible the design of complex heterogeneous nano-structures.

In some variants of the multi-dimensional structure, the multi-dimensional structure of DNA and nanoparticle-functionalized g5p comprises a DNA structure having multiple branches of ssDNA, a peptide conjugated to g5p, and nanoparticles bound specifically to the peptide. In preferred embodiments the g5p is bound to the ssDNA. In this manner, a complex structure of DNA and nanoparticle-functionalized g5p is formed.

In some variants of the multi-dimensional scaffold, the multi-dimensional DNA scaffold comprises two strands of ssDNA (strands 1 and 2) mutually bound by sequences of C-ssDNA at a first locus; two other strands of ssDNA (strands 3 and 4) mutually bound by sequences of C-ssDNA at a second locus; strands 2 and 3 are mutually bound by sequences of C-ssDNA at the second locus; and g5p bound to at least two of the strands of ssDNA at one or more points between the bound loci.

In preferred embodiments of the multi-dimensional scaffold, the multi-dimensional scaffold further contains at least one nanoparticle bound to at least one of the g5p. In more preferred embodiments of the multi-dimensional scaffold, at least one nanoparticle is bound to at least one region of DNA.

In some embodiments a goal is to improve DNA- and protein-induced nano-scale materials and sensors. In some embodiments this may be achieved by: association of two anti-parallel ssDNA by g5p; and dissociation of g5p from ssDNA by hybridization of complementary DNA or nucleic acids.

In some embodiments, a g5p-mediated DNA assemblage comprises non-complementary DNA or RNA strands bound to a nucleotide binding protein. In this manner, an assemblage is formed.

g5p is encoded by filamentous bacteriophages where it cooperatively binds to ssDNA to form precursors for the assembly of phage particles. In vitro, g5p forms a homodimer which will non-specifically bind two anti-parallel ssDNAs, inducing helical rod-like structures with 8~9 nm outer diameter. The number of nucleotides bound per g5p monomer is 2~4 and depends on binding conditions, including the protein to nucleotide ratio. The binding affinity of g5p to ssDNA, about $10^5$ to about $10^6$ $M^{-1}$, depends on the sequence of ssDNA and the salt concentration, with preferential binding to structured DNA such as hairpins and G-quadruplexes. The g5p protein's DNA binding properties for assembly and disassembly of ssDNA-conjugated nanoparticles are thus exploited.

Figure 6:
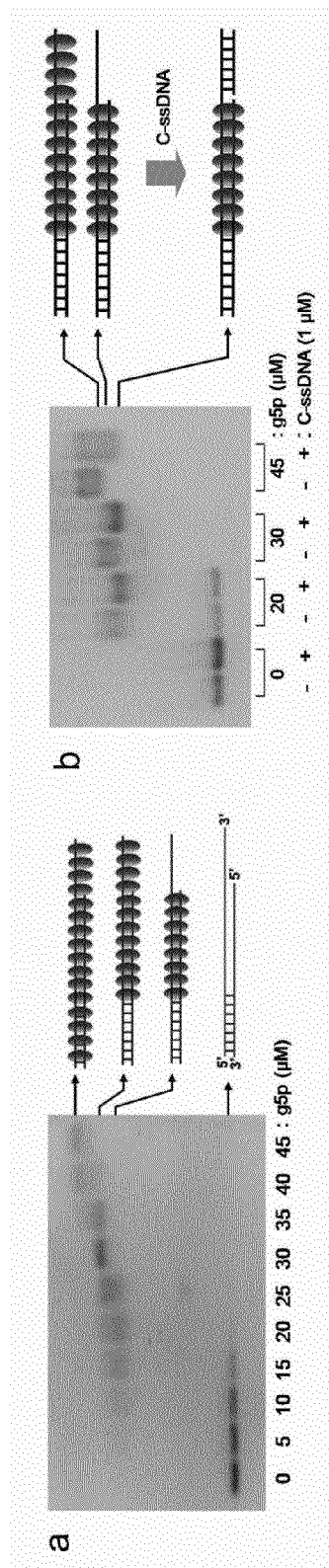
FIGS. 6A and 6B show the results of electrophoretic mobility shift assays.

To study the distinct binding properties of g5p and its preferential DNA topology, an exemplary DNA structure with three distinct regions has been designed: a 19 base paired double-stranded DNA (dsDNA) region, followed by a 32 nucleotide anti-parallel poly-T ssDNA region, and a 3' extended ssDNA tail of 15 nucleotides. The DNA structure (1 μm) was titrated with g5p (in 10 mM Tris-HCl, pH=7.4, 200 mM NaCl), and g5p binding was studied using the electrophoretic mobility shift assay. Three distinct stages of g5p binding were observed, suggesting its sequential binding (FIG. 6A). Since g5p has a much lower affinity to dsDNA than to ssDNA at high salt concentration, the following order of occupancy is hypothesized: binding to the anti-parallel ssDNA region with a large shift of the DNA band at 10 μM g5p, followed by binding to the ssDNA tail, and finally to dsDNA at g5p concentrations over 35 μM. Thus, g5p binds to ssDNA regions before it binds to the dsDNA region, and its binding affinity for the anti-parallel region is slightly higher than for the ssDNA tail. To study the effect of g5p association on forming dsDNA heteroduplexes, and confirm the proposed binding order to the ssDNA regions, an equal amount (1 μM) of C-ssDNA that can hybridize to the ssDNA tail was added. After C-ssDNA addition, the two different stages of band shift observed with 20 μM and 30 μM g5p changed to an identical position with higher mobility (FIG. 6B), indicating that the first stage of the band shift results from binding of g5p to the anti-parallel ssDNA region. Smearing of the band after C-ssDNA addition at 45 μM g5p supports g5p binding to dsDNA at this concentration. By comparing the intensity of the band in the presence of 30 μM g5p to the band under control conditions without g5p, the hybridization efficiency for C-ssDNA to the g5p-complexed ssDNA tail was determined to be approximately 82%, indicating effective DNA hybridization without significant inhibition by g5p.

Figure 7A:
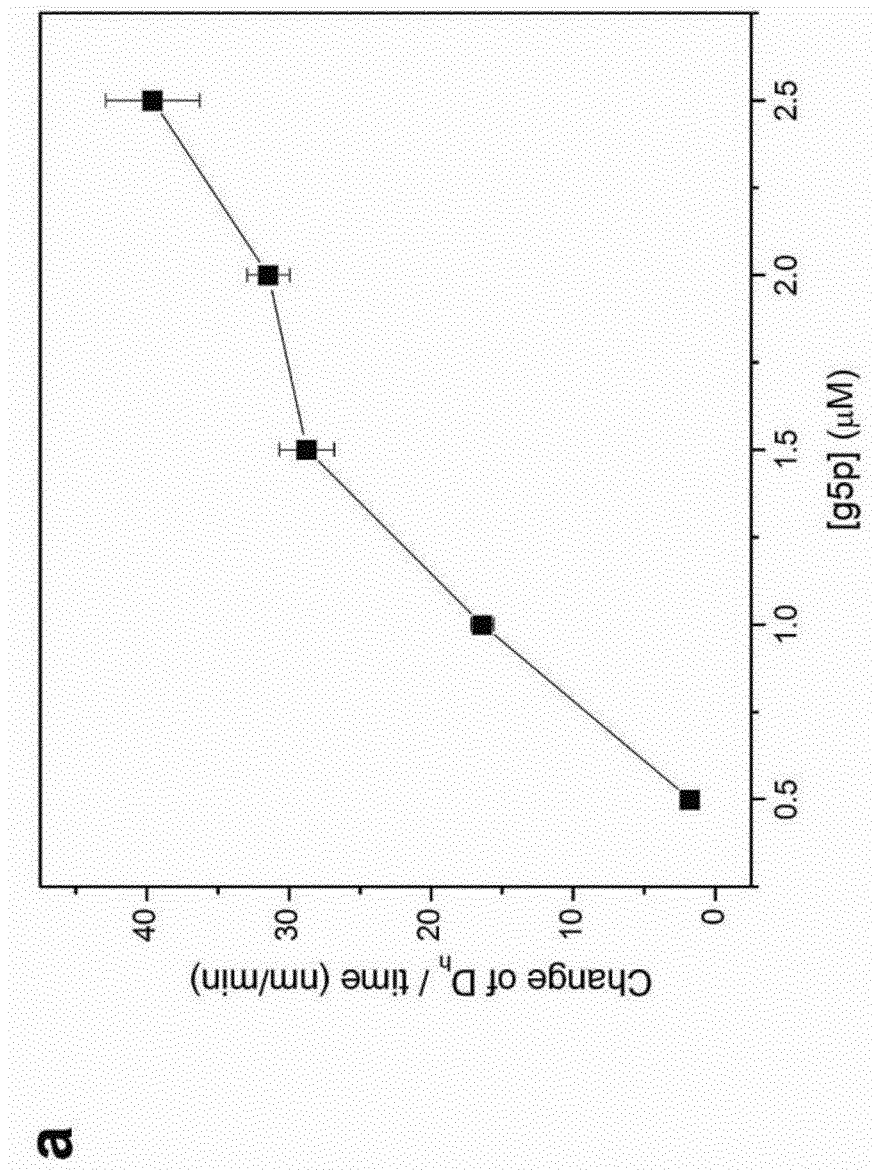
FIGS. 7A, 7B, and 7C are data from g5p-mediated assembly of ssDNA-conjugated gold particles.
Figure 7B:
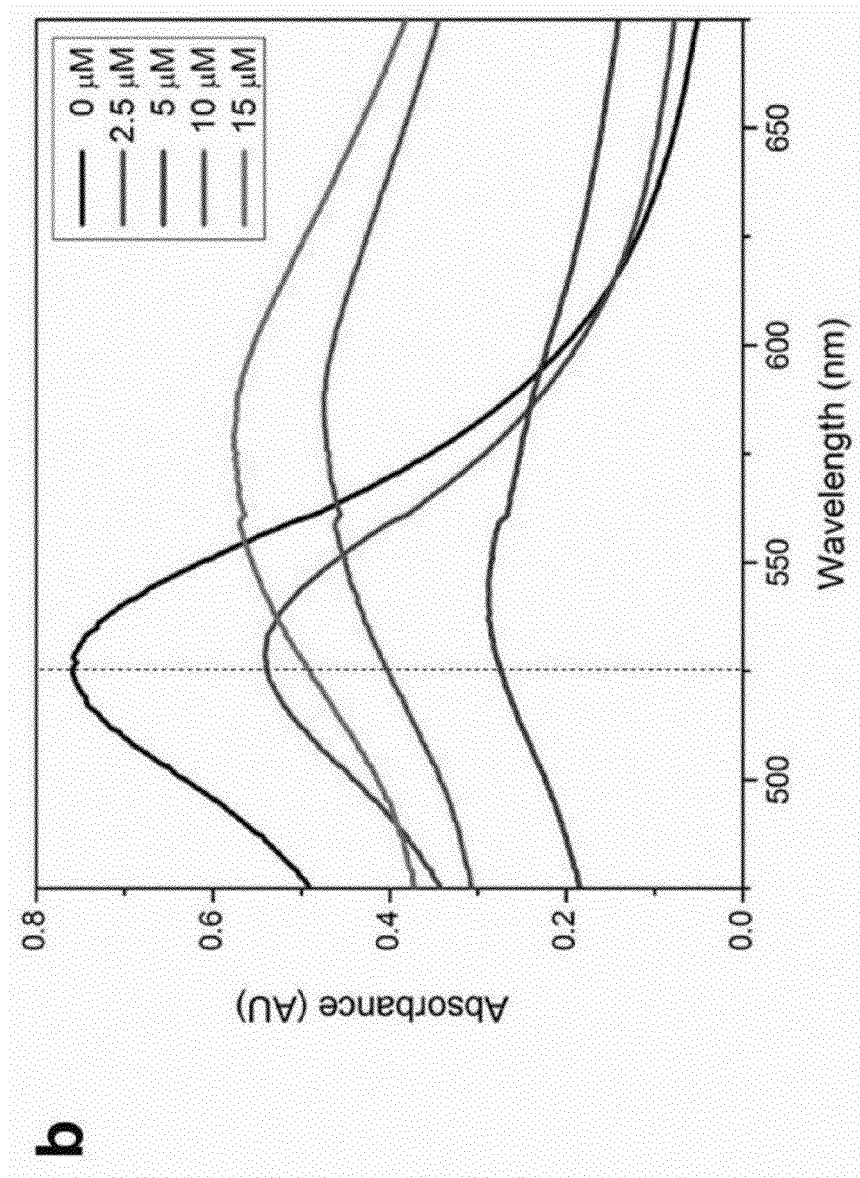
Figure 7C:
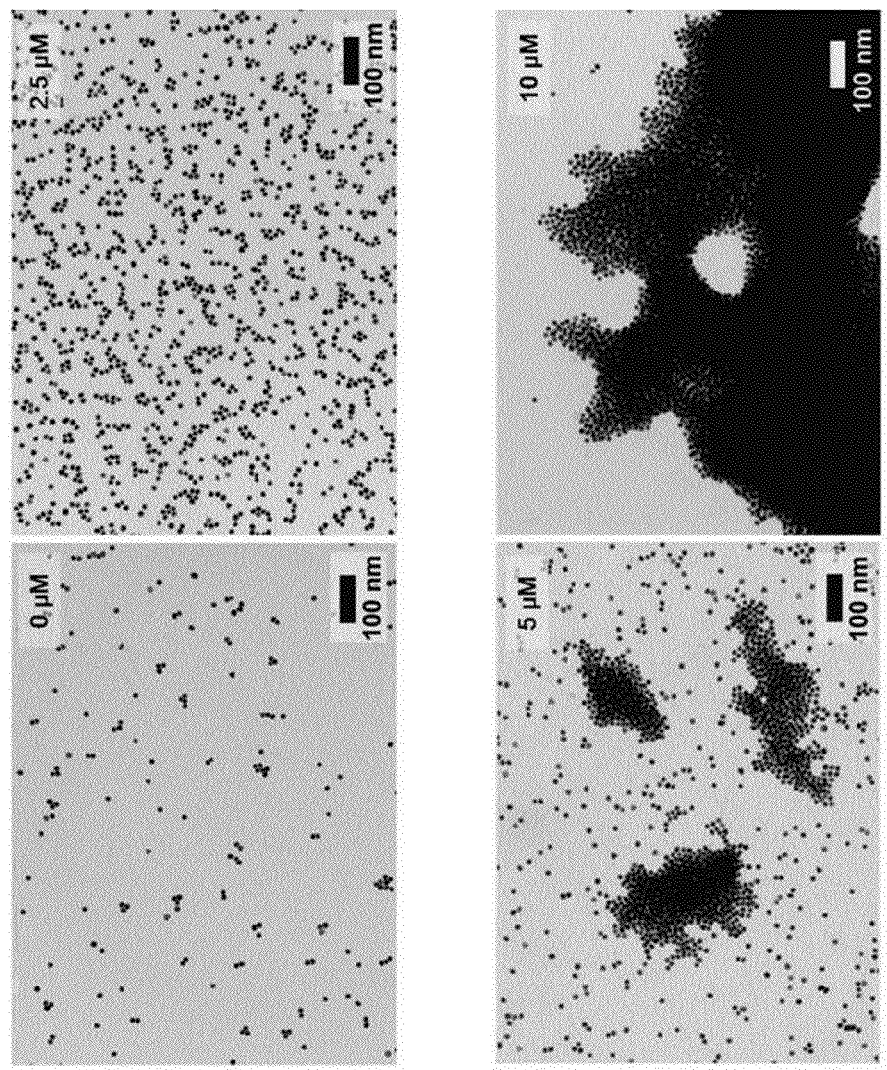
Figure 8A:
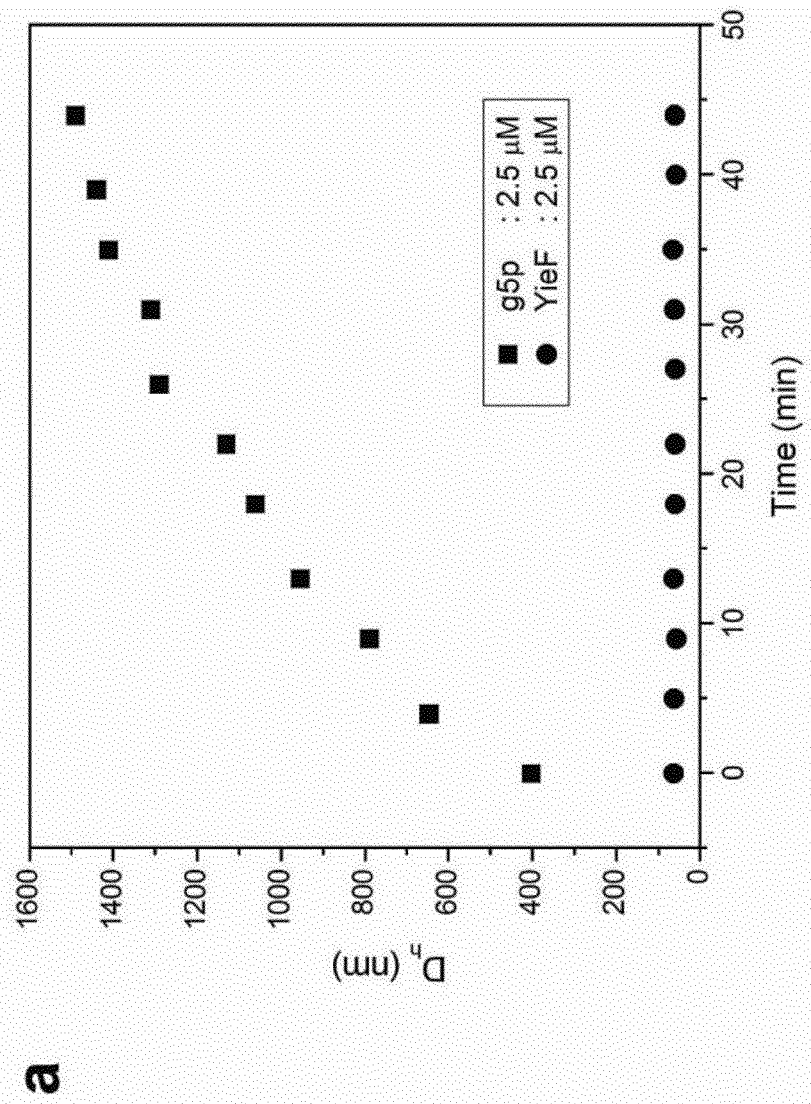
FIGS. 8A and 8B show results of dynamic light scattering and ultraviolet-visible analyses of ssDNA-conjugated gold particles.
Figure 8B:
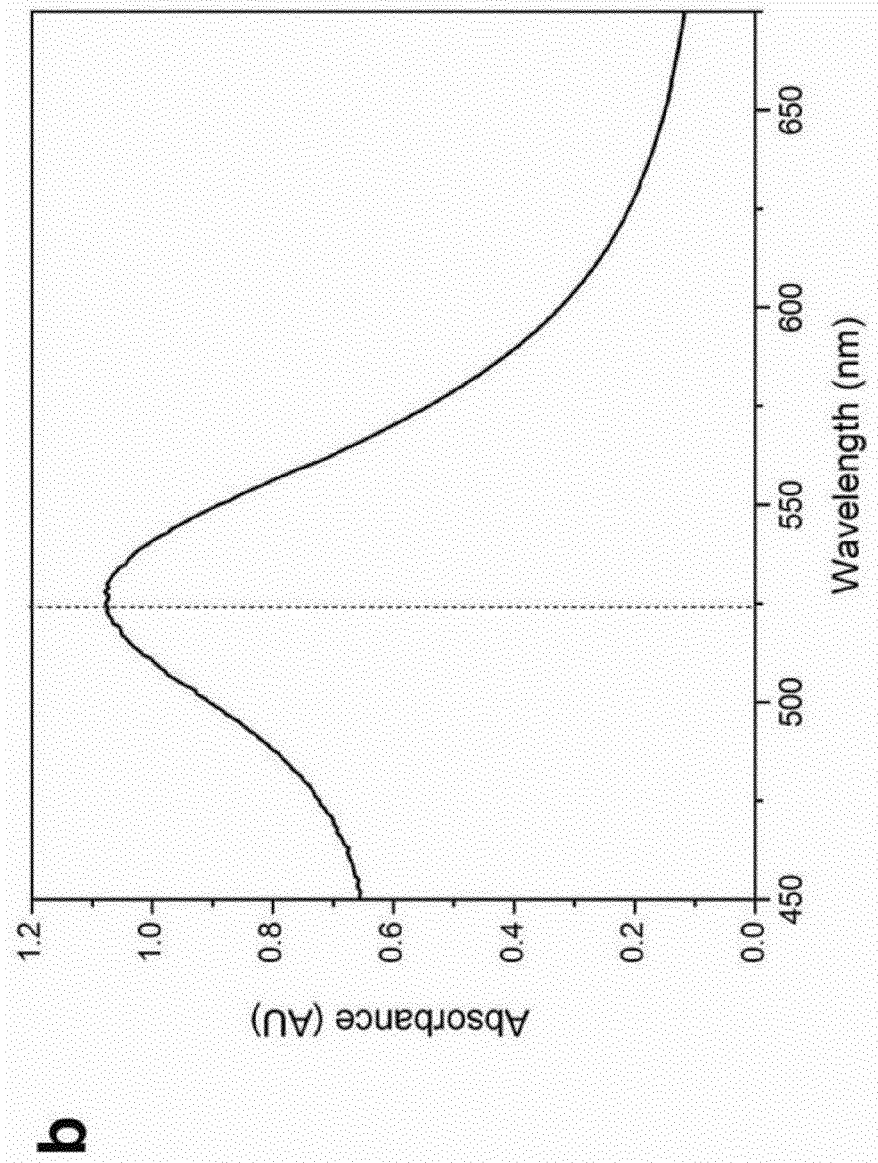

To exploit g5p's ability to assemble ssDNA-conjugated nanoparticles, gold nanoparticles (Au) encapsulated with approximately 50 copies of ssDNA (5'-HS-C3H6-$(T)_{15}$-TAACCTAACCTTCAT-3') (SEQ ID NO. 1) were synthesized, and g5p-mediated assembly of the ssDNA-conjugated gold nanoparticles (ssDNA-Au) was tested. Dynamic light scattering (DLS) was used to measure changes of the hydrodynamic diameter value ($D_h$), which is related to aggregate size, interparticle interactions, and geometry. FIG. 7A shows that the initial assembly rate of $D_h$ during incubation of g5p and the ssDNA-Au for 20 minutes was highly sensitive to the g5p concentration, indicating g5p-dependent assembly of ssDNA-Au. No assembly was observed in the absence of g5p. To investigate assembly of ssDNA-Au (20 nM) during prolonged incubation (~24 hours) with a series of g5p concentrations, the ssDNA-Au surface plasmon (SP) resonance band was studied using ultraviolet-visible spectrophotometry (UV-vis). The SP band is associated with isolated Au and assembled nanostructures. After adding increased g5p concentrations, the SP band at 525 nm of isolated ssDNA-Au was red-shifted with band broadening, indicative of either a decrease in interparticle distances or an increase of aggregate size (FIG. 7B). The higher extinction intensity observed over 10 μM g5p is due to a decrease of the solution's turbidity resulting from the formation of larger aggregates. Both DLS and UV-vis results confirm the assembly of ssDNA-Au by g5p. The sizes and morphologies of the g5p-mediated ssDNA-Au assemblies were studied using transmission electron microscopy (TEM) (FIG. 7C). The aggregate sizes were found to increase with increased g5p concentrations, as suggested by DLS and UV-vis, whereas the numbers of non-assembled particles decreased, suggesting that the size of aggregates can be simply controlled by the g5p concentration. Polyhistidine-tagged YieF protein (MW=20 KDa) was used as a negative control, for which no aggregation of particles was observed during DLS and UV-vis studies (FIGS. 8A and 8B). These results clearly illustrate that g5p can be used for the controlled assembly of ssDNA-Au by changing the protein-nanoparticle ratios.

Figure 9:
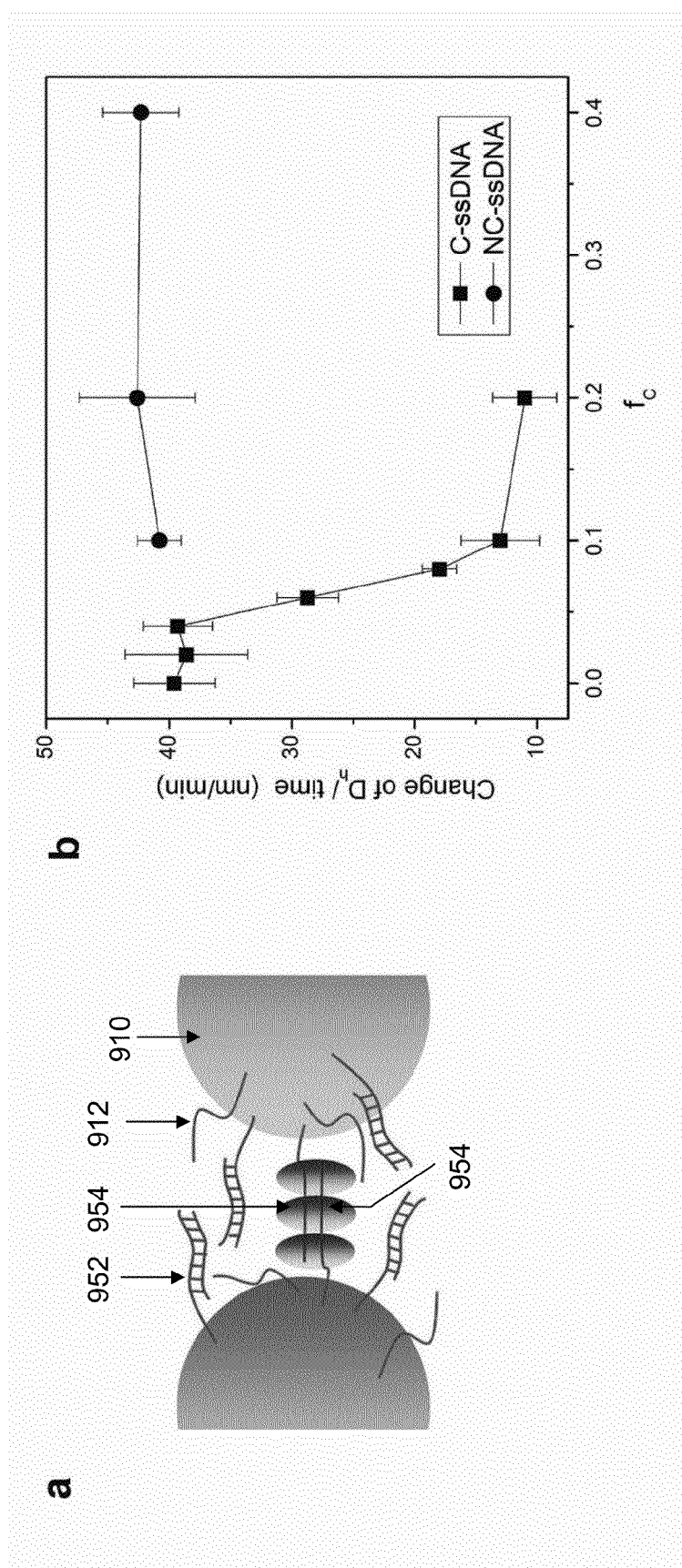
FIGS. 9A and 9B show a schematic of a g5p protein-mediated assembly of ssDNA-conjugated gold particles, and changes of the hydrodynamic diameter value of such assemblies, respectively.

To investigate inhibitory effects of dsDNA on aggregate formation, the ssDNA-capping of the particles was first partially hybridized with C-ssDNA (5'-ATGAAGGTTAG-GTTA-3') (SEQ ID NO. 2) before g5p-mediated assembly was initiated (FIG. 9A). Changes in assembly rate in response to C-ssDNA concentrations were studied using DLS (FIG. 9B). The assembly rate dramatically dropped when the fraction of C-ssDNA to ssDNA on Au ($f_C$) was larger than about 0.05. This large inhibitory effect caused by a low density of dsDNA suggests large steric hindrance for g5p-mediated assembly of ssDNA-Au. A non-complementary ssDNA (NC-ssDNA; 5'-AATATTGATAAGGATAGC-3') (SEQ ID NO. 3) was used as a control to eliminate any inhibitory titration effects caused by binding of g5p to ssDNA in solution. The effect of the NC-ssDNA on the assembly rate was found to be statistically insignificant (FIG. 9B).

g5p bound to ssDNA can be replaced by C-ssDNA hybridization (FIG. 6B). This should result in dissociation of the aggregates, which can be used to detect the presence of C-ssDNA. To prove this, aggregates were prepared by incubation of ssDNA-Au (10 nM) and g5p (5 μM) for about 24 hours, after which the aggregates were incubated with C-ssDNA for about 12 hours at room temperature. Colorimetric changes indicative of aggregate size changes were monitored using UV-vis. The peak position blue-shifted over approximately 200 nM of C-ssDNA ($f_C$=~0.4) (FIG. 10A), indicating dissociation of small clusters and release of individual particles. In the NC-ssDNA control the peak intensity decreased slightly but no shift in peak position was observed (FIG. 10B); NC-ssDNA caused the aggregates to divide into smaller clusters, but not to the level of individual particles. A TEM image of the sample with 200 nM C-ssDNA clearly shows the dissociation with dispersed particles (FIG. 10C), whereas this dissociation was not observed for the sample with NC-ssDNA.

Figure 11:
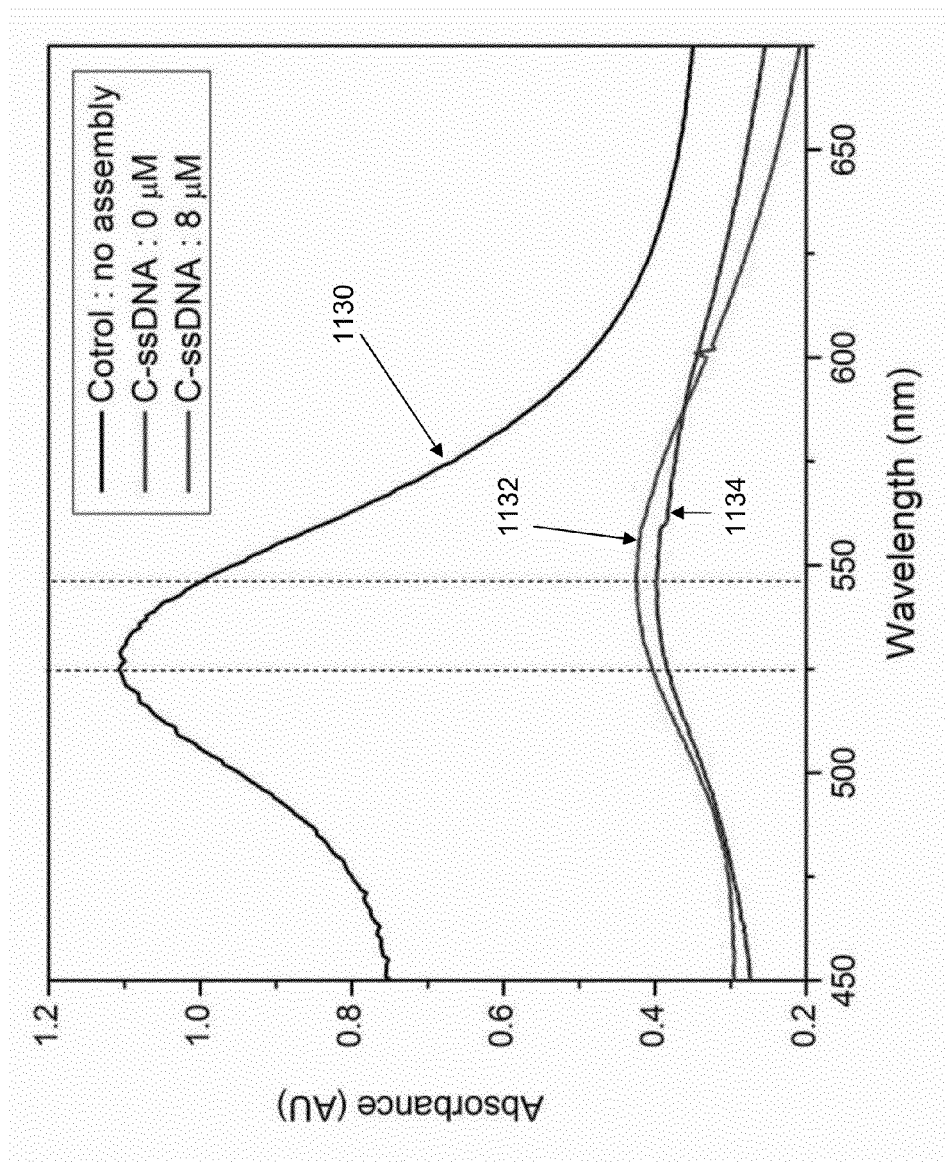
FIG. 11 shows the effect of the addition of C-ssDNA on gold particle aggregates.

DNA-controlled dissociation of aggregates is a useful property of the g5p-ssDNA system. To demonstrate this, gold nanoparticles were assembled into aggregates by a conventional hybridization method incubating ssDNA-Au particles and their target particles (C-ssDNA-Au) that were encapsulated by C-ssDNA (5'-HS-$C_3H_6$-$(T)_{15}$-ATGAAGGTTAG-GTTA-3') (SEQ ID NO. 4). Once formed, dissociation of the aggregates was studied as a function of the addition of increased C-ssDNA concentrations. However, no aggregate dissociation was observed till $f_C$ approached about 16 (FIG. 11).

For the correct assembly of ssDNA-Au and C-ssDNA-Au particles, properties inherent to the DNA sequences, such as G-C content, often control the assembly process. The inventive method for controllable assembly of non-complementary ssDNA-conjugated nanoparticles, using g5p as the driving force, is novel. Control of assembly kinetics and dissociation of particle aggregates can be obtained via sequence-specific hybridization with C-ssDNA, while the size of aggregates is controlled by adjustment of the g5p concentration.

Another aspect of the invention includes a molecular switch. In a variant of the molecular switch comprises a fluorescent quenched "off" position and a fluorescent emission "on" position. In preferred embodiments of the fluorescent quenched "off" position, a first ssDNA is bound to fluorescein at the 5' end forming a fluorescein-ssDNA strand, a second ssDNA bound to DABCYL at the 3' end to form a ssDNA-DABCYL strand, the fluorescein-ssDNA strand and the ssDNA-DABCYL strand bound together with g5p. The switch can be turned "on" by hybridizing a complementary ssDNA or ssRNA to either the fluorescein-ssDNA strand or the ssDNA-DABCYL strand. In this manner, the fluorescein quencher is removed and fluorescence detection is enabled, turning the switch from an "off" position to an "on" position.

In another variant of the molecular switch, an activated, "on", switch comprises a segment of dsDNA; a first strand of ssDNA bound to one of the two strands of the dsDNA and to DABCYL at respective ends. The switch also includes a second strand of ssDNA bound to the other of the two strands of the dsDNA and to fluorescein at respective ends, the two strands of ssDNA non-complementary each to the other. The switch is turned "off" by attaching g5p to at least one pair of DABCYL-tipped and fluorescein-tipped ssDNA strands, such that fluorescence from the fluorescein is quenched during attachment via g5p.

Peptides have been successfully used for the construction of nanostructures and self-assembly of inorganic nanoparticles. Genetic engineering of the g5p protein to display peptides provides further opportunities to design sophisticated nanomaterials. The sensitive disassembly of the aggregates in the presence of C-ssDNA without the need for thermal treatment, as would be the case for nanoparticle aggregates based on complementary DNAs, demonstrates the great potential of this approach for the design of biologically functional, hybrid materials and DNA-based biosensors; while thermal treatment of these hybrid materials will often result in the irreversible inactivation of functional moieties, such as proteins, the addition of a C-ssDNA should not affect their activities. We also note that this new assembly approach, based on gyp and ssDNA, can be extended to other kinds of nanomaterials, including carbon nanotubes, semi-conductors, and magnetic nanoparticles.

FIG. 1 shows a prior art method for self-assembly and disassembly of ssDNA-conjugated nanoparticles. This traditional method for self-assembly of ssDNA-conjugated nanoparticles by hybridization with complementary DNA, and disassembly by increase of the temperature above the melting temperature ($T_m$) of the hybridized DNA. Nanoparticles 110 are functionalized with ssDNA sequences 112, at least some of which are complementary to each other. The complementary DNA sequences 114 of the nanoparticles are allowed to hybridize 116, resulting in self-assembly of the nanoparticles. The assembled nanoparticles 118 then form an aggregate 120, which may be disassembled 122 by increasing the temperature above the melting temperature 124 of the dsDNA strands 126 resulting in disaggregation and disassembly 128 of the functionalized nanoparticles.

Figure 2:
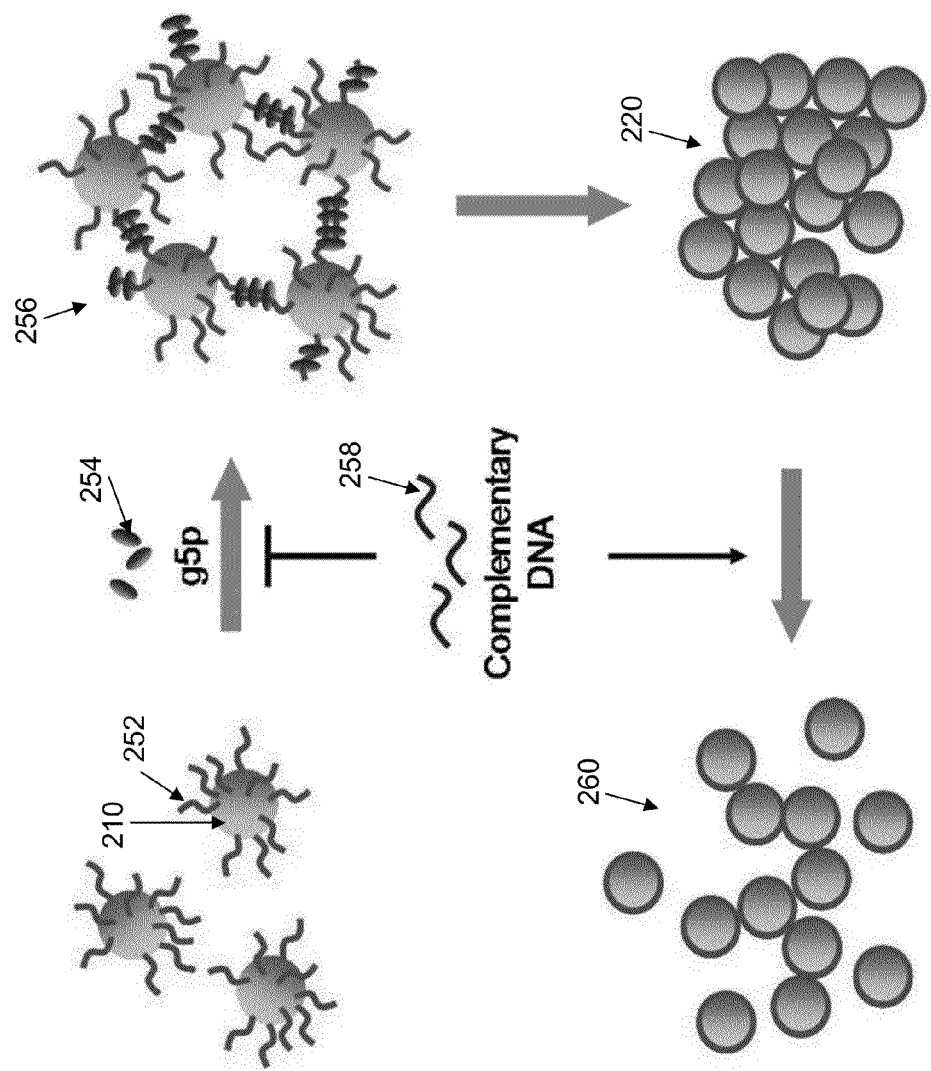
FIG. 2 depicts a controllable g5p-mediated assembly and disassembly technique.

FIG. 2 depicts a controllable gyp-mediated assembly and disassembly of non-complementary ssDNA-conjugated nanoparticles Inhibition of assembly and induction of disassembly by hybridization with complementary DNA may be observed. Nanoparticles 210 are functionalized with non-complementary DNA 252. g5p 254 is added and the nanoparticles self-assemble into an assemblage 256 and, if desired, into an aggregate 220. The addition of DNA complementary to the sequences functionalizing the nanoparticles 258 results in disaggregation and disassembly 260 of the nanoparticles.

These assembly/disassembly processes may also work in reverse. FIG. 3 shows a sketch of ssDNA-mediated assembly and disassembly of g5p-conjugated nanoparticles. Here nanoparticles 310 are functionalized with g5p 354. Single-stranded DNA 312 is added to the solution and the functionalized nanoparticles self-assemble. When C-ssDNA 314 is added, the nanoparticles disassemble.

Figure 4:
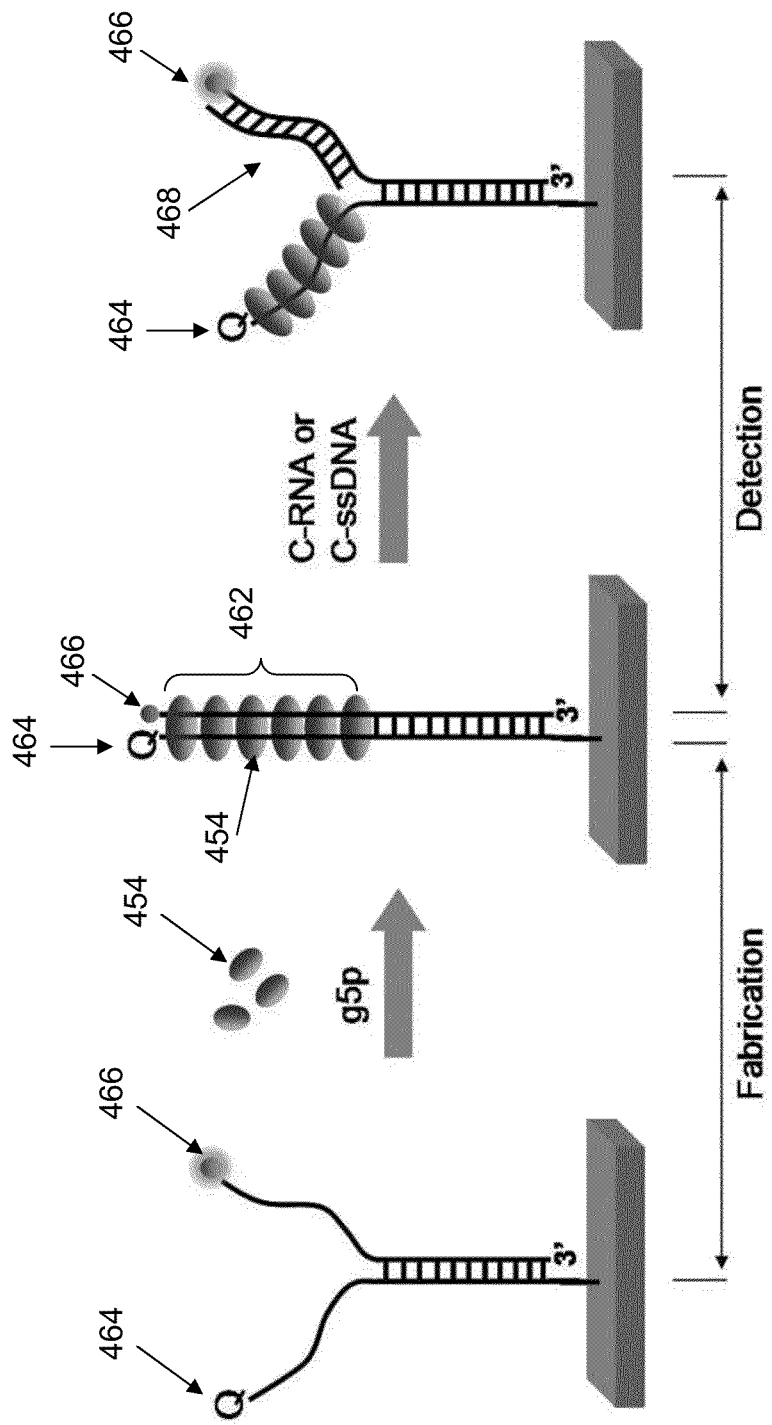
FIG. 4 depicts the functioning of a g5p-mediated molecular switch.

FIG. 4 depicts the functioning of a g5p-mediated molecular switch. Binding of g5p 454 to an anti-parallel ssDNA region 462 causes DABCYL (Q) 464 to move close to fluorescein 466, resulting in quenching of fluorescence. This may be seen as the fabrication of a molecular switch, in a normally "off" position, or detector. The fluorescent emission can be recovered by hybridization of complementary RNA (C-RNA) or C-DNA 468 with either of the anti-parallel strands. This process corresponds to detection of the target or turning "on" the molecular switch.

FIG. 5 shows self-assembly of nanoparticles at ordered peptide-conjugated g5p and DNA. A DNA structure 570, shown here with four branches of ssDNA, is assembled by peptide-conjugated g5p 554, and nanoparticles 510 may be ordered by binding specifically to the peptides. This may result in arbitrarily structured nanoparticle architectures.

FIGS. 6A and 6B show the results of electrophoretic mobility shift assays. Titration of a DNA fragment with three regions of distinct topology is shown in FIG. 6A. The regions are 19 base pairs of dsDNA, anti-parallel poly-T ssDNA (32 bases), and a ssDNA tail of 15 bases. A model of the binding is depicted in the right panel. The bottom of the illustration shows the structured DNA with the three regions. FIG. 6B depicts the mobility shift of the g5p complexes upon binding of C-ssDNA to the ssDNA tail, with a model of the binding in the right panel.

FIGS. 7A, 7B, and 7C are data from g5p-mediated assembly of ssDNA-conjugated gold particles. The chart in FIG. 7A shows the change in the hydrodynamic diameter value ($D_h$) during incubation of ssDNA-Au (5 nm) and g5p, as a function of the concentration of g5p (in µM) using a DLS analysis technique. $D_h$ is seen to increase monotonically with the concentration of g5p. FIG. 7B shows changes in the UV-vis spectra as the concentration of g5p changes from zero to 15 µM in a solution of 10 mM Tris-HCl, pH 7.44, 200 mM NaCl. Not only does the intensity change, but the peak also shifts to longer wavelengths (experiences a red-shift) as the concentration of g5p increases.

FIG. 7C is a series of TEM images of the morphology of nanoparticle assemblages as the concentration of g5p is increased from zero to 10 µM in a solution of 10 mM Tris-HCl, pH 7.44, 200 mM NaCl. With no g5p the nanoparticles are sparsely and relatively uniformly spaced over the substrate. Increasing the concentration to 2.5 µM results in larger, more densely spaced nanoparticle assemblies. Further increasing the concentration of g5p to 5 µM induces the beginning of agglomeration of the particles. Virtually complete agglomeration of nanoparticles is shown for a concentration of 10 µM.

FIGS. 8A and 8B show results of DLS and UV-vis analyses of ssDNA-conjugated gold particles. In FIG. 8A DLS shows $D_h$ for 5 nm ssDNA-Au incubated with 2.5 µM g5p and 2.5 µM YieF. $D_h$ for ssDNA-Au in the presence of YieF showed no change, while that incubated with g5p increased to nearly 1.5 µm. FIG. 8B shows UV-vis spectra after incubation for approximately 24 hours of 20 nm ssDNA-Au with 15 µM YieF, showing a peak position of about 525 nm.

FIGS. 9A and 9B show a schematic of a g5p-mediated assembly of ssDNA-conjugated gold particles, and changes of the hydrodynamic diameter value of such assemblies, respectively. FIG. 9A is a schematic illustration of preferential binding of g5p 954 to anti-parallel ssDNA 912 over dsDNA 952 FIG. 9B shows the change in $D_h$ per minute as a function of $f_C$ (the number fraction of C-ssDNA in the solution, i.e., the number of C-ssDNA divided by the total number of ssDNA on the gold nanoparticles 910). The figure shows the changes of $D_h$ during (2.5 µM) g5p protein-mediated assembly of ssDNA-conjugated gold particles (ssDNA-Au≈5 nM) which were prehybridized with C-ssDNA.

Figure 10A:
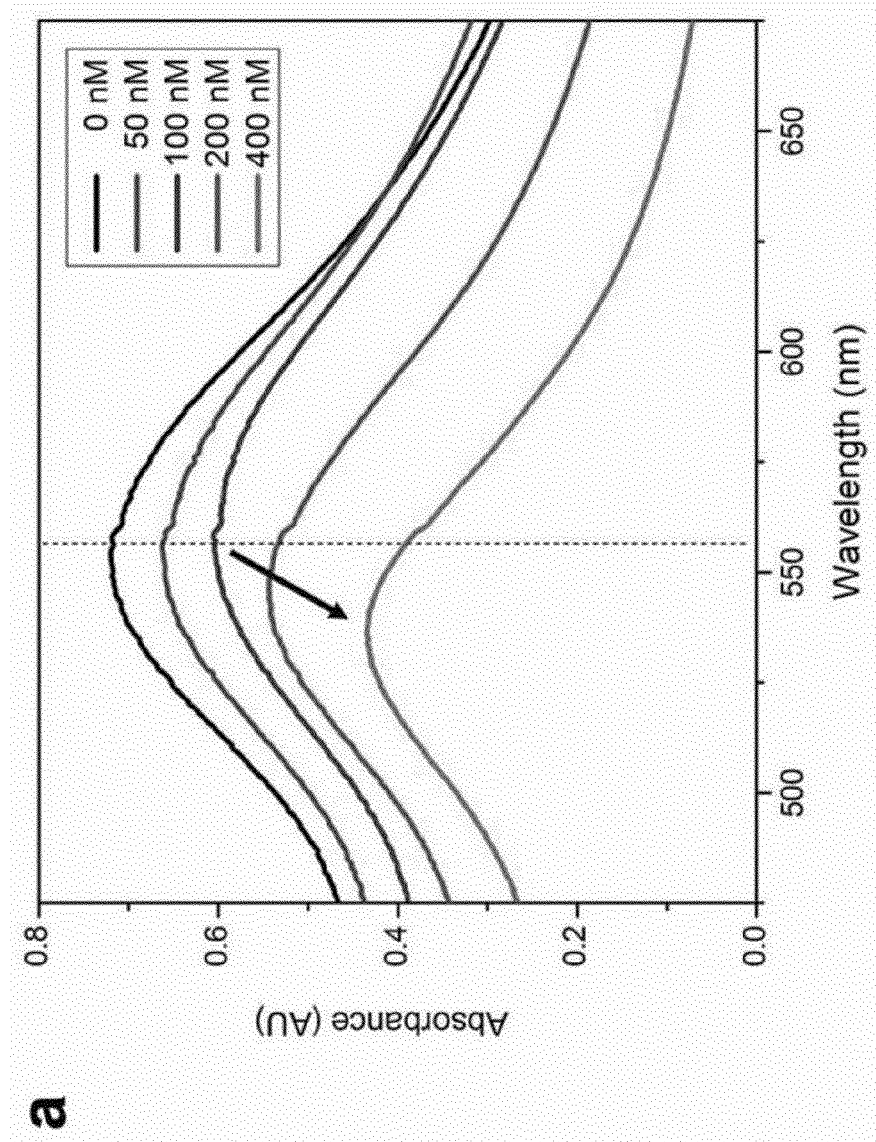
FIGS. 10A, 10B, and 10C depict the decomposition of g5p-mediated ssDNA-conjugated gold particle aggregates.
Figure 10B:
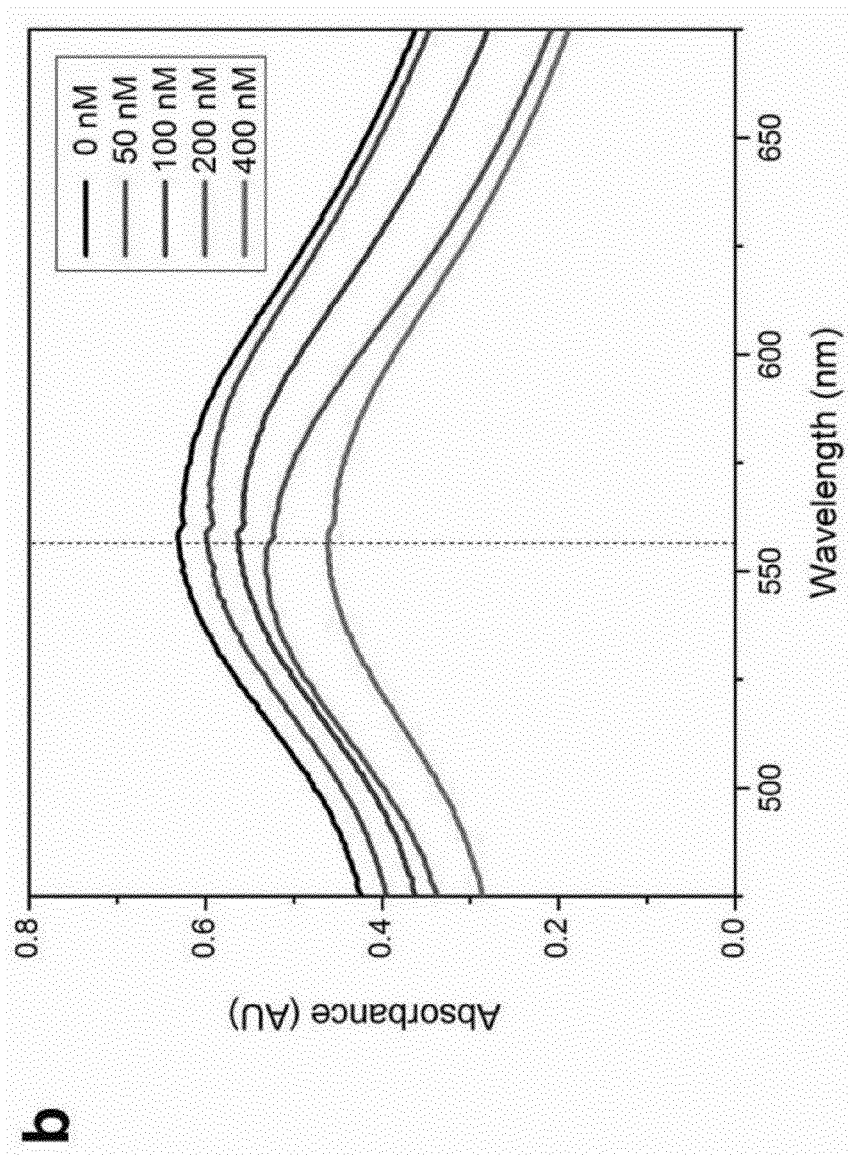
Figure 10C:
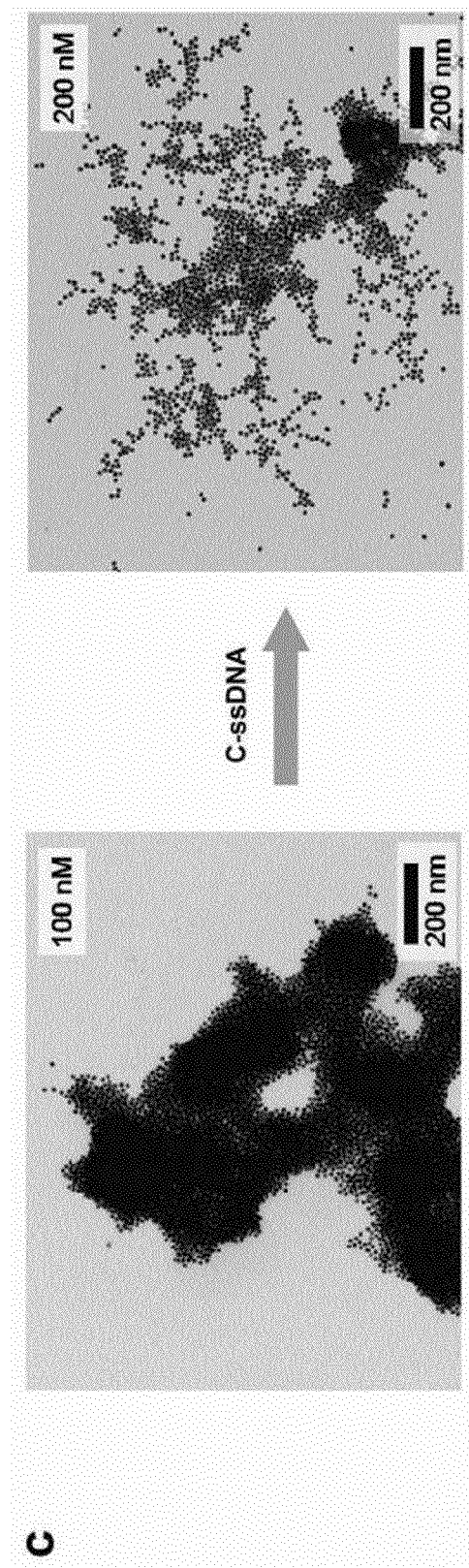

FIGS. 10A, 10B, and 10C depict the decomposition of g5p-mediated ssDNA-conjugated gold particle aggregates when C-ssDNA is added. FIGS. 10A and 10B show UV-vis data from nanoparticle aggregates (10 nM ssDNA-Au and 5 µM g5p) after about 12 hours' incubation with C-ssDNA (FIG. 10A) or NC-ssDNA (FIG. 10B). As seen in the figures, ssDNA-Au complexes incubated with C-ssDNA experience a shift in the peak absorbance wavelength while those incubated with NC-ssDNA do not. FIG. 10C shows TEM images of the sample after incubation with 100 nM ($f_c$=~0.2) and 200 nM C-ssDNA ($f_c$=~0.4).

FIG. 11 shows the effect of the addition of C-ssDNA on gold particle aggregates. Gold nanoparticles were assembled into aggregates by a conventional hybridization method incubating ssDNA-Au and their target particles (C-ssDNA-Au) that were encapsulated with the complementary ssDNA. Single-stranded DNA-Au (10 nM) and C-ssDNA-Au (10 nM) were incubated for ~24 hours in 10 mM Tris-HCl, pH 7.4, 200 mM NaCl, causing a peak shift from ~525 nm (control 1130) to ~548 nm (0 µM 1132). Recovery of the peak shift was not observed after incubation with C-ssDNA (8 µM 1134).

Example Methods

The following precise descriptions are provided merely as concrete examples. No endorsement of any product or manufacturer is implied by its inclusion herein. Specific trade names, models, and manufacturers are provided only for specificity and may be substituted for by equipment of similar capability and reagents of similar quality. In addition, all measurements of time, quantity, concentration, etc. are given to within experimental and human error.

Protein Preparations

The g5p gene of bacteriophage M13 (New England Biolabs (NEB)) was amplified with polymerase chain reaction (PCR) using the primers 5'-TAATTCCATATGAT-TAAAGTTGAAATTAAACCA-3' (SEQ ID NO. 5) and 5'-TAGCTTGCTCTTCCGCACTTAGCCG-GAACGAGGCG-3' (SEQ ID NO. 6). This generally results in a DNA fragment flanked by NdeI and SapI restriction sites. The PCR product was digested with NdeI and SapI (NEB) and ligated into the pET-30b vector (Novagen). After the confirmation of the sequence, the recombinant plasmid was introduced into BL21-DE3 electroporation competent cell, using the Gene Pulser Xcell System (Bio-Rad). G5p protein expression was induced by addition of Isopropyl β-D-1-thiogalactopyranoside (IPTG) (Sigma) in lysogeny broth (LB) medium with Kanamycin (100 µg/ml) (Sigma). After the expression period, cells were sonicated, and the His-tagged g5p protein was purified using a Ni-NTA column (Qiagen). Further g5p purification was obtained using fast protein liquid chromatography (FPLC) (AKTA explorer, GE Healthcare) with a Sephacryl S-200 high resolution sizing column (Amersham Biosciences). A purity of >95% was obtained, as was determined by analysis of the protein bands using the Quantity One software (Bio-Rad), after staining with Coomassie Blue on a 15% SDS-polyacrylamide gel. Molar extinction coefficient of 7450 $M^{-1}$ $cm^{-1}$ was used to determine protein concentration. The YieF protein was prepared as described previously by Zhang, Y. B., et al., *Functionalized carbon nanotubes for detecting viral proteins.* Nano Letters, 7(10): pp. 3086-3091, 2007, which is hereby incorporated by reference in its entirety.

Electrophoretic Mobility Shift Assay

The DNA for the binding study was obtained by annealing of two ssDNA with sequences, 5'-GACCACATACCGCAC-CATC(T)$_{32}$CTGCTACGAGACTTC-3' (SEQ ID NO. 7) and 5'-(T)$_{32}$GATGGTGCGGTATGTGGTC-3' (SEQ ID NO. 8), respectively. The annealed DNA (1 µM) was incubated with g5p at 37° C. for 10 minutes. The DNA was visualized by ethidium bromide staining after agarose gel (2.5%) electrophoresis. The C-ssDNA, with sequence 5'-GAA GTC TCG TAG CAG-3' (SEQ ID NO. 9), was added to the complex of g5p and the annealed DNA, and was incubated at 37° C. for 15 minutes before the electrophoresis. Relative intensities of the DNA bands were analyzed after ethidium bromide staining Characterization UV-Visible spectra were obtained using a PerkinElmer Lambda 35 spectrometer. DLS was measured using a Malvern Zetasizer ZS instrument that is equipped with a 633 nm laser and a backscattering detector at 173°. To visualize ssDNA-Au, a JEOL 1300 TEM was operated at 120 kV. TEM samples were prepared by incubation of samples on a carbon-coated copper grid for 10 minutes and washed with distilled water two times.

Given the teaching herein, the inventors and other practitioners in the art may expand the approach to more complex DNA-g5p structures for assembly of nanoparticles. Display of functional peptide at C-terminal of g5p may allow for biologically active nanomaterials. In addition, the use of other classes of nanoparticles (semiconductive, magnetic) is considered for more potential applications. The work described may be further exploited for the development of biosensors, including the development of approaches for microarray design.

This method makes it possible to control both assembly and disassembly of DNA-conjugated nanoparticles at biological conditions without thermal treatments, to easily incorporate proteins into DNA based nanostructures implying great potential to design complex nanomaterials, and to design approaches for the detection of nucleotide sequences (DNA, RNA) without the need for their labeling.

While the foregoing description has been made with reference to individual embodiments of the invention, it should be understood that those skilled in the art, making use of the teaching herein, may propose various changes and modifications without departing from the invention in its broader aspects. For example gene proteins other than g5p may be used. In another embodiment, the invention may be used for detecting chemical species for security applications.

The foregoing description being illustrative, the invention is limited only by the claims appended hereto.

The invention claimed is:

1. A controllable and reversible nanoparticle assembly comprising, nanoparticles encapsulated with non-complementary DNA and/or RNA, the noncomplementary DNA and/or RNA bound by a nucleotide binding protein to form a nanoparticle assembly, wherein the nucleotide binding protein is gene-5 protein of bacteriophage M13.

2. The controllable and reversible nanoparticle assembly according to claim 1, wherein the nanoparticle assembly is disassembled by further combining the nanoparticle assembly with DNA and/or RNA complementary to the non-complementary DNA and/or RNA.

3. The controllable and reversible nanoparticle assembly according to claim 1, wherein the nanoparticle is a metal.

4. The controllable and reversible nanoparticle assembly according to claim 3, wherein the metal is selected from the group consisting of gold, silver, and platinum.

5. The controllable and reversible nanoparticle assembly according to claim 4, wherein the metal is gold.

6. The controllable and reversible nanoparticle assembly according to claim 1, wherein the nanoparticle is a semiconductor.

7. The controllable and reversible nanoparticle assembly according to claim 6, wherein the semiconductor is selected from the group consisting of cadmium selenide, cadmium sulfide, zinc sulfide, and gallium arsenide.

8. The controllable and reversible nanoparticle assembly according to claim 1, wherein the nanoparticle is magnetic.

9. The controllable and reversible particle assembly according to claim 8, wherein the nanoparticle is iron oxide.

10. The controllable and reversible nanoparticle assembly according to claim 1, wherein the DNA and/or RNA are single stranded.

11. The controllable and reversible nanoparticle assembly according to claim 1, wherein the DNA and/or RNA include a double stranded region.

12. A g5p-mediated DNA assemblage comprising, non-complementary DNA or RNA strands, the non-complementary DNA or RNA strands bound and a nucleotide binding protein, thereby forming an assemblage, wherein the nucleotide binding protein is gene-5 protein of bacteriophage M13.

13. The g5p-mediated DNA assemblage according to claim 12, wherein the DNA or RNA is single stranded.

* * * * *